US010791960B2

(12) United States Patent
Adamko et al.

(10) Patent No.: US 10,791,960 B2
(45) Date of Patent: Oct. 6, 2020

(54) DIAGNOSIS OF ASTHMA VERSUS CHRONIC OBSTRUCTIVE PULMONARY DISEASE (COPD) USING URINE METABOLOMIC ANALYSIS

(71) Applicant: UNIVERSITY OF SASKATCHEWAN, Sasakatoon (CA)

(72) Inventors: Darryl Adamko, Saskatoon (CA); Anas El-Aneed, Saskatoon (CA)

(73) Assignee: University of Saskatchewan, Saskatoon (CA)

( * ) Notice: Subject to any disclaimer, the term of this patent is extended or adjusted under 35 U.S.C. 154(b) by 343 days.

(21) Appl. No.: 15/579,524

(22) PCT Filed: Jun. 3, 2016

(86) PCT No.: PCT/CA2016/050637
§ 371 (c)(1),
(2) Date: Dec. 4, 2017

(87) PCT Pub. No.: WO2016/191885
PCT Pub. Date: Dec. 8, 2016

(65) Prior Publication Data
US 2018/0153438 A1 Jun. 7, 2018

Related U.S. Application Data

(60) Provisional application No. 62/170,848, filed on Jun. 4, 2015.

(51) Int. Cl.
*G01N 33/493* (2006.01)
*G01N 33/68* (2006.01)
*A61B 5/08* (2006.01)
*G16H 10/40* (2018.01)
*G16H 50/20* (2018.01)
*G16H 50/70* (2018.01)
*G16H 20/10* (2018.01)

(52) U.S. Cl.
CPC ............. *A61B 5/08* (2013.01); *G01N 33/493* (2013.01); *G01N 33/6893* (2013.01); *G16H 10/40* (2018.01); *G16H 20/10* (2018.01); *G16H 50/20* (2018.01); *G16H 50/70* (2018.01); *G01N 2570/00* (2013.01); *G01N 2800/122* (2013.01)

(58) Field of Classification Search
CPC ............... A61B 5/08; G01N 2570/00; G01N 2800/122; G01N 33/48; G01N 33/493; G01N 33/6893; G01N 33/6884; G16H 10/40; G16H 20/10; G16H 50/20; G16H 50/70; Y10T 436/24

USPC ............... 436/63, 86, 89, 161, 173
See application file for complete search history.

(56) References Cited

U.S. PATENT DOCUMENTS

| | | | |
|---|---|---|---|
| 9,823,204 B2* | 11/2017 | McClay | G01N 33/57423 |
| 2010/0136600 A1* | 6/2010 | Slupsky | G01N 24/08 435/29 |
| 2011/0238319 A1* | 9/2011 | Adamko | G01N 24/08 702/19 |
| 2012/0021532 A1* | 1/2012 | Eszter | G01N 33/6893 436/501 |
| 2013/0149389 A1* | 6/2013 | Flora | G01N 33/6893 424/600 |
| 2013/0183684 A1* | 7/2013 | Gibson | G01N 33/6842 435/7.4 |
| 2019/0285632 A1* | 9/2019 | Malcolm | G01N 33/56983 |

FOREIGN PATENT DOCUMENTS

| | | |
|---|---|---|
| WO | WO 2010/020058 | 2/2010 |
| WO | WO 2011/041892 | 4/2011 |

OTHER PUBLICATIONS

International Search Report prepared by the Canadian Intellectual Property Office dated Aug. 22, 2016, for International Application No. PCT/CA2016/050637.
Written Opinion prepared by the Canadian Intellectual Property Office dated Aug. 22, 2016, for International Application No. PCT/CA2016/050637.
Adamko, et al., "Asthma and Lower Airway Disease: Metabolomic Profiling of Asthma and Chronic Obstructive Pumonary Disease: A Pilot Study Differentiating Diseases," Journal of Allergy and Clinical Immunology vol. 136, No. 3, Sep. 2015, pp. 571-580.
Guo et al., "Differential 12C-/13C-Isotope Dansylation Labeling and Fast Liquid Chromatography/Mass Spectrometry for Absolute and Relative Quantification of the Metabolome," Analytical Chemistry vol. 81, No. 10, May 15, 2009, pp. 3919-3932.
Guo, "High-Performance Isotope Labeling for Profiling Carboxylic Acid-Containing Metabolites in Biofluids by Mass Spectrometry," Analytical Chemistry vol. 82, No. 21, Nov. 1, 2010, pp. 8789-8793.
Luscek et al., "Urine Metabolomics in Hermorrhagic Shock: Normalization of Urine in the Face of Changing Intravascular Fluid Volume and Perturbations in Metabolism," Journal of Bioanalysis & Biomedicine, vol. 3, No. 2, 2011, pp. 38-48.

* cited by examiner

*Primary Examiner* — Maureen Wallenhorst
(74) *Attorney, Agent, or Firm* — Sheridan Ross P.C.

(57) ABSTRACT

Described are methods and uses employing metabolomic data to diagnose an asthma disease state or a Chronic Obstructive Pulmonary Disease (COPD) state. Further described are methods of uses of employing metabolomic data to distinguish between asthma and COPD. In particular, urinary metabolomic profiles are employed to enable differential diagnosis of asthma and COPD.

10 Claims, 11 Drawing Sheets

DIAGNOSIS OF ASTHMA VERSUS CHRONIC OBSTRUCTIVE PULMONARY DISEASE (COPD) USING URINE METABOLOMIC ANALYSIS

CROSS REFERENCE TO RELATED APPLICATIONS

This application is a national stage application under 35 U.S.C. 371 of PCT Application NO. PCT/CA2016/050637, having an international filing date of Jun. 3, 2016, which designated the United States, which PCT application claimed the benefit of U.S. provisional patent application Ser. No. 62/170,848 filed Jun. 4, 2015, both of which are hereby, incorporated by reference herein in their entirety.

TECHNICAL FIELD

The present application relates to diagnosis of pulmonary disorders, and more particularly, to improved diagnosis of asthma versus chronic obstructive pulmonary disease (COPD) using metabolomic analysis.

BACKGROUND

Diseases of the respiratory system are among the leading diseases in terms of their impact on society. According to the 1998/99 National Population Health Survey, there were around 2,474,400 Canadians diagnosed with asthma and 498,900 with COPD. These illnesses resulted in 454 and 9,398 deaths, respectively. COPD is the 5th leading cause of death in Canada, and the only one that is increasing in prevalence. The prevalence of asthma is increasing worldwide, and it is the most common chronic disease of childhood. These conditions place a significant burden on the healthcare system, accounting for over $4 billion annually in direct and indirect costs.

A feature common to most diseases of the respiratory system is some form of lung inflammation. Lung inflammation consists of specific inflammatory cells and by products generated by cellular activity. Thus, specific lung diseases are often diagnosed not only by their clinical presentation, but also by the type of inflammation measured. Inflammatory cells release enzymes and other proteins in the airway, which can be measured and are specific to the cell type (i.e. mast cell tryptase or eosinophil cationic protein). The pathology of asthma is different from that seen in COPD, and the degree of inflammation and cellular damage varies with disease severity. For example, patients with asthma often have sputum samples positive for cells called eosinophils, and those with COPD or pneumonia present with increased sputum neutrophils. Differentiating asthma from other causes of chronic airflow limitation such as Chronic Obstructive Pulmonary Disease (COPD) can be difficult in a typical outpatient setting.

In addition, the degree of inflammation and cellular damage varies with asthma or COPD severity.

The treatments for each disease are designed to address this inflammation (i.e. corticosteroids or biologics versus antibiotics).

Unfortunately for clinicians, detecting this inflammation in individual patients is often difficult. Instead, clinicians rely on physiological (i.e. spirometry, peak flow, airway hyperreactivity (AHR)) or functional measurements (i.e. symptoms, or quality of life) to assess response to therapy. These tests, while useful, appear to be somewhat insensitive to changes in inflammatory status that later become clinically relevant.

While accurate airway inflammation measurements from bronchoscopy are possible, it is invasive and unavailable in the daily clinical setting. Thus, research has focused on non-invasive measures of inflammation such as induced sputum, eNO, and various inflammatory markers in body fluids. While experience with sputum has shown valuable results, significant barriers remain to its use clinically, including limited availability in most centers and the inability of young children and even many adults to expectorate. Exhaled NO (eNO) overcomes some of these barriers; however, while eNO shows correlation with asthma inflammation and outcomes experimentally, it requires time, co-operation, age greater than 4 years and, unless very carefully performed, may measure sinus rather than airway values. Ultimately, eNO still lacks the sensitivity and specificity of induced sputum. While other tests for asthma inflammation in blood or urine have been studied, i.e. urine leukotrienes, or eosinophil protein X, they lack the sensitivity required for clinical practice. Overall, a simple, non-invasive, readily available and sensible test for patients with airway inflammation is currently not widely available.

Using objective measurements of airway inflammation to guide asthma therapy can produce superior therapeutic results compared with traditional measures alone (e.g., symptoms and lung function).

For clinicians in a typical outpatient setting, detecting airway inflammation is often difficult. As such, differentiating asthma from other respiratory diseases like Chronic Obstructive Pulmonary Disease (COPD) can be difficult as both have somewhat similar clinical presentations. Objective measurements for differentiation of asthma and COPD are not used in a typical doctors office. Most clinicians continue to rely upon patient history and examination before making a diagnosis and administering trials of therapy. If the incorrect diagnosis is made, then the prescribed treatment will likely be ineffective, and exposing patients to un-necessary side-effects and the patients respiratory problem will likely persist costing the health care system money and causing longer suffering by the patient.

Metabolomics is the study of metabolic pathways and biochemical molecules created in a living system. By measuring changes in metabolites, biochemical effects induced by a disease or its therapeutic intervention can be determined. However, typically it is not just a change in one metabolite that allows for identification of a disease state or the effects of therapeutic intervention. Rather, a combination of metabolites must be identified and analysed in order for relevant information to be obtained.

Accordingly, there remains a need to provide a reliable and easy-to-use method of objective measurements for improved diagnosis of asthma versus chronic obstructive pulmonary disease (COPD) that can overcome the limitations of the prior art.

SUMMARY

A metabolomic approach for improved diagnosis of asthma versus chronic obstructive pulmonary disease (COPD) is provided. Multivariate statistical analysis of data from urine can identify distinct metabolomic profiles that correlate with the clinical phenotypes of asthma versus COPD.

Analysis of metabolites in urine, as provided herein, can have the ability differentiate patients with asthma versus COPD both in the Emergency Department (ED) at the time of exacerbation and in follow-up post treatment.

Broadly stated, in some embodiments, a method is provided for diagnosing an asthma disease state in a subject comprising: obtaining metabolomic data on an obtained biological sample from the subject to obtain a subject profile; b. performing a statistical analysis on the metabolomic data to compare the subject profile to a predetermined asthma disease state profile and to a predetermined Chronic Obstructive Pulmonary Disease (COPD) disease state profile, wherein the analysis does not comprise identification of components of the biological sample; and c. providing a diagnosis of the asthma disease state when the statistical analysis identifies the subject profile as more similar to the predetermined asthma disease state profile than to the predetermined COPD disease state profile.

Broadly stated, in some embodiments, a method is provided for diagnosing an asthma disease state in a subject comprising: measuring a concentration of at least 11 of the metabolites as disclosed herein in an obtained biological sample from the subject to determine a subject profile; comparing the subject profile, by a statistical analysis, to a predetermined asthma disease state profile and to a predetermined Chronic Obstructive Pulmonary Disease (COPD) disease state profile; and providing a diagnosis of the asthma disease state when the statistical analysis identifies the subject profile as more similar to the predetermined asthma disease state profile than to the predetermined COPD disease state profile.

Broadly stated, in some embodiments, a method is provided for diagnosing a Chronic Obstructive Pulmonary Disease (COPD) disease state in a subject comprising: a. obtaining metabolomic data on an obtained biological sample from the subject to obtain a subject profile; b. performing a statistical analysis on the metabolomic data to compare the subject profile to a predetermined asthma disease state profile and to a predetermined Chronic Obstructive Pulmonary Disease (COPD) disease state profile, wherein the analysis does not comprise identification of components of the biological sample; and c. providing a diagnosis of the COPD disease state when the statistical analysis identifies the subject profile as more similar to the predetermined COPD disease state profile than to the predetermined asthma disease state profile.

Broadly stated, in some embodiments, a method is provided for diagnosing a Chronic Obstructive Pulmonary Disease (COPD) disease state in a subject comprising: a. measuring a concentration of at least 11 of the metabolites as disclosed herein in an obtained biological sample from the subject to determine a subject profile; b. comparing the subject profile, by a statistical analysis, to a predetermined asthma disease state profile and to a predetermined Chronic Obstructive Pulmonary Disease (COPD) disease state profile; and c. providing a diagnosis of the COPD disease state when the statistical analysis identifies the subject profile as more similar to the predetermined COPD disease state profile than to the predetermined asthma disease state profile.

Broadly stated, in some embodiments, a method is provided for creating a predetermined profile for differentiating between an asthma disease state and a Chronic Obstructive Pulmonary Disease (COPD) disease state in a subject comprising: measuring the concentration of at least 11 of the metabolites as disclosed herein in each of a plurality of urine samples obtained from asthma patients and COPD patients; performing a statistical analysis on the concentration values of (a) to differentiate between the asthma disease state and the COPD disease state.

Broadly stated, in some embodiments, a diagnostic model is provided for differentiating between an asthma disease state and a Chronic Obstructive Pulmonary Disease (COPD) disease state in a subject, the diagnostic model comprising at least 11 of the metabolites as disclosed herein.

Broadly stated, in some embodiments, a use of a diagnostic model as described herein is provided for diagnosing an asthma disease state and/or a COPD disease state in a subject in a subject.

In some embodiments, a computer readable medium is provided, the computer readable medium comprising instructions for carrying out the methods and/or the uses according to the methods and/or the uses as described herein.

In some embodiments the biological sample is urine.

In some embodiments the statistical analysis id a partial least squares discriminant analysis.

In some embodiments the concentration of at least one metabolite is determined using one or more or a combination of spectrometric and spectroscopic techniques selected from the group consisting of liquid chromatography, gas chromatography, high performance liquid chromatography, capillary electrophoresis, mass spectrometry, liquid chromatography-mass spectrometry, gas chromatography-mass spectrometry, high performance liquid chromatography-mass spectrometry, capillary electrophoresis-mass spectrometry, raman spectroscopy, near infrared spectroscopy, and nuclear magnetic resonance spectroscopy.

In some embodiments a method of quantifying at least one metabolite with a phenol or amine functional group is provided comprising preparing a urine sample from a patient comprising, diluting the sample with ACN, buffer and $^{12}C$-DNS-CI, heating the sample; adding NaOH to the sample; further heating the sample; acidifying the sample; increasing the volume of the sample; spiking the sample with $^{13}C$-IS, and increasing the volume of the sample with 50% ACN; running the prepared urine sample through the mass spectrometer to obtain a measurement of the at least one metabolite with a phenol or amine functional group; determining the concentration of creatinine in the sample; and normalizing the measurement of the at least one metabolite with a phenol or amine functional group using the concentration of creatinine in the sample.

In some embodiments a method of quantifying at least one metabolite with a carboxylic acid functional group is provided, the method comprising preparing a urine sample from a patient comprising, diluting the sample with ACN; combining the sample with TEA and $^{12}C$-DmPA, heating the sample; cooling the sample to room temperature; and diluting the sample with formic acid, ACN and $^{13}C$-DmPA standard solution; running the prepared urine sample through the mass spectrometer to obtain a measurement of the at least one metabolite with a carboxylic acid functional group; determining the concentration of creatinine in the sample; and normalizing the measurement of the at least one metabolite with a carboxylic acid functional group using the concentration of creatinine in the sample.

In some embodiments a method of diagnosing asthma versus COPD is provided comprising obtaining a biological sample from a patient; identifying the concentration of metabolites present in the biological sample using the method of either one or both of the quantification methods described above to create a subject profile; comparing the subject profile, by a statistical analysis, to a predetermined asthma disease state profile and to a predetermined Chronic Obstructive Pulmonary Disease (COPD) disease state profile; and providing a diagnosis of asthma or COPD when the statistical analysis identifies the subject profile as more similar to one of the predetermined disease state profiles than to the other predetermined disease state profile.

In some embodiments the metabolomic data includes information on at least 11 metabolites.

In some embodiments the at least 11 metabolites include 3-Hydroxyisovalerate, Glutamine, Arginine, Lactic acid, Glycolate, Tyrosine, 2-oxoglutarate, Glycine, Histidine, 1-methylhistamine and Taurine.

In some embodiments the at least 11 metabolites further include any number of the VIP metabolites.

In some embodiments the method may further include administering a treatment for asthma or COPD to the subject, as appropriate based on the diagnosis. In some embodiments the treatment for asthma comprises one or more of high dose corticosteroids and biological therapy targeting asthmatic inflammation. In some embodiments the treatment for COPD comprises one or more of anti-muscarinic inhaler, antibiotics, lung surgery and lung transplantation.

In some embodiments the step of obtaining metabolomic data is performed using the method of either one or both of the quantification methods described above.

In some embodiments the step of measuring the concentration of at least 11 metabolites is performed using the method of either one or both of the quantification methods described above.

DETAILED DESCRIPTION OF EMBODIMENTS

Figure 1:
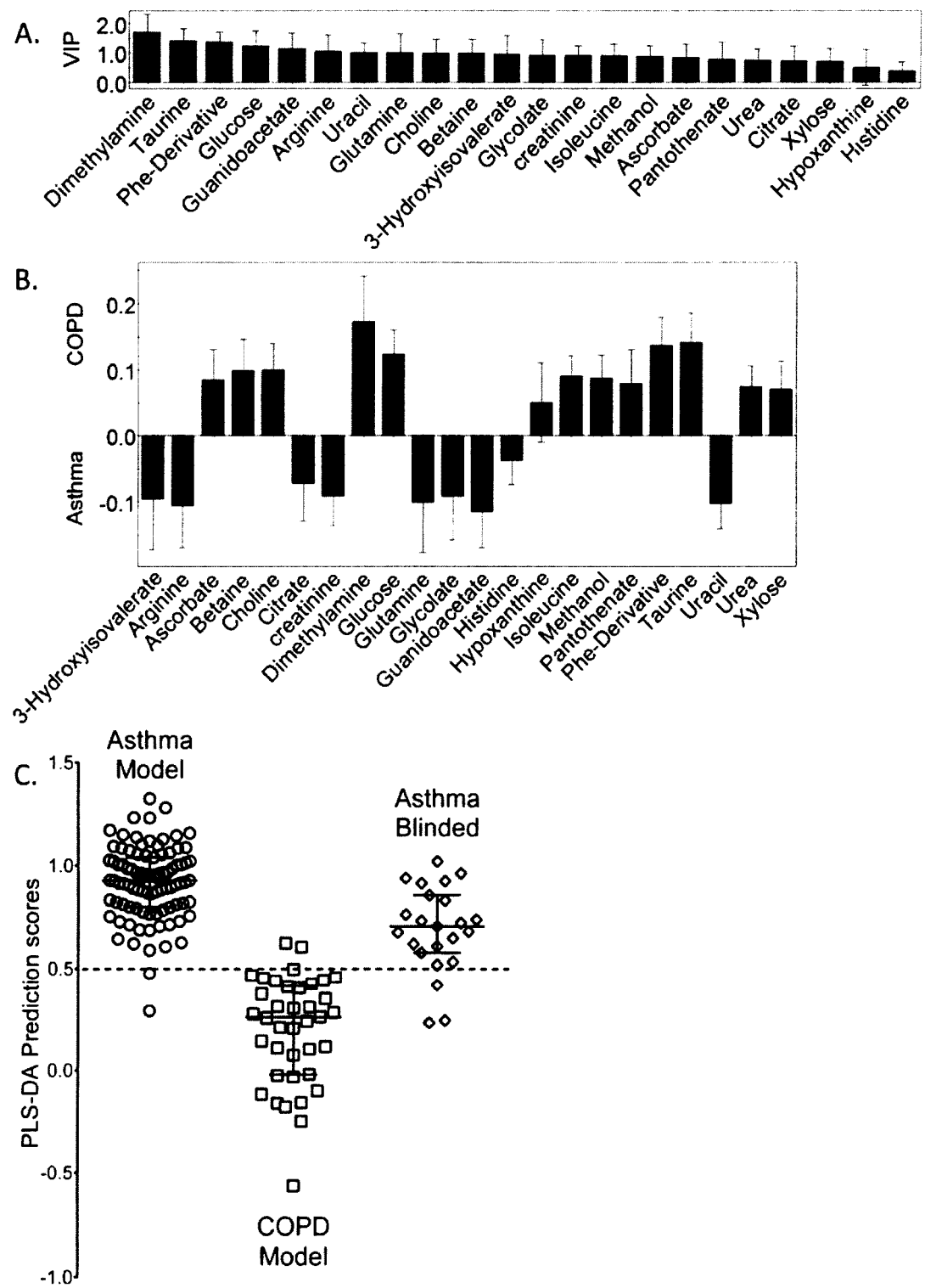
FIGS. 1A-1C depict an embodiment of a metabolomic model of exacerbation of asthma versus COPD in the Emergency Department (ED).

Metabolomics is the study of metabolic pathways and biochemical molecules created in a living system. By measuring changes in metabolites, biochemical effects induced by a disease or its therapeutic intervention can be determined. Methods of identifying and quantifying metabolites can include spectrometric and spectroscopic techniques including but not limited to liquid chromatography, gas chromatography, high performance liquid chromatography, capillary electrophoresis, mass spectrometry, liquid chromatography-mass spectrometry, gas chromatography-mass spectrometry, high performance liquid chromatography-mass spectrometry, capillary electrophoresis-mass spectrometry, raman spectroscopy, near infrared spectroscopy, and nuclear magnetic resonance spectroscopy.

1H-nuclear magnetic resonance (NMR) spectroscopy, for example, can be used to quantify metabolites within a biofluid. NMR is a useful technology because it provides both qualitative and quantitative measurements, while simultaneously studying a number of compounds in the same biologic fluid. Once a metabolite has been identified, other techniques such as mass spectrometry could be used to quantify metabolites. Urine is a primary candidate biological fluid owing to its ease of collection in patients of all ages, low cell and protein content, and rich chemical composition.

Mass Spectrometry (MS) is another technology which has the ability to measures thousands more metabolites than NMR, but its methodology makes screening more difficult. As discussed below, for absolute quantification of metabolites, MS requires specific methods designed for each structurally-related metabolite. Once a set of candidate biomarkers is proposed, it is necessary to obtain isotope labeled standards to confirm metabolite identity, and then develop calibration curves using novel methods in order to quantify concentrations. This requires an immense of amount of work. Therefore, it is preferred to initially identify metabolites using NMR and then confirm their presence and quantification using MS.

COPD and asthma involve a number of unique cellular pathways, but these pathways can still converge to produce a similar clinical outcome. Symptoms or lung function measurements may not differentiate asthma from COPD (e.g. airway remodeling in asthma gives a pattern of fixed obstruction). Thus, a unique combination of metabolites, rather than a single metabolite, can be required to differentiate these complex pathologies. Using only one factor to separate groups requires large consistent differences with minimal measurement overlap. This has not been demonstrated for previous single biomarkers (e.g. eNO, urine leukotrienes, eosinophil cationic protein). Airway dysfunction, increased work of breathing, and hypoxemia will cause cellular stress inside and outside the lung. Using urine as a sample biofluid can be less invasive than samples from the airway. The ability to use urine makes the methodology advantageously applicable to most clinical settings, especially for children.

The metabolic activity of patients with asthma would be expected to differ from those with COPD. As a result, the profile of metabolites present in a biological sample from a patient with asthma would be expected to differ from the profile of metabolites present in a biological sample from a patient with COPD. Specific methods and processes employed to identify and quantify particular metabolites and/or metabolite profiles that are relevant to asthma and COPD have been developed and improved are disclosed herein.

Differentiating asthma from other causes of chronic airflow limitation such as Chronic Obstructive Pulmonary Disease (COPD) is difficult in outpatient settings. The inflammation of asthma typically is different compared to COPD, and the degree of inflammation and cellular damage varies with asthma severity. Therefore, the diagnosis and treatments prescribed differ in important ways.

In general terms, the diagnosis of asthma, COPD and/or the identification of asthma versus COPD can be performed using the following steps. A set of metabolomic data is obtained on a biological sample from a subject in order to obtain a subject profile. Statistical analysis can then be performed on the metabolomics data which compares the subject profile to predetermined metabolomic models representing either the asthma or COPD disease state. Based on the results of the statistical analysis, a diagnosis of a disease state can be made possible.

Table 1 shows the metabolites which have been identified as and Variables of Importance Plot (VIP) metabolites and which can be used in any number of combinations to create a metabolomic model.

TABLE 1

| VIP metabolites | |
|---|---|
| 1 | Pantothenic acid |
| 2 | Cis/Trans aconitic acids |
| 3 | 3 Hydroxy 3 Methyl glutaric acid |
| 4 | Lactic acid |
| 5 | Ethanolamine |
| 6 | Pyroglutamic acid |
| 7 | Glycolic acid |
| 8 | Tryptophane |
| 9 | Creatinine |
| 10 | 2-oxoglutaric acid |
| 11 | Valine |
| 12 | 2-hydroxy isobutyric acid |
| 13 | 1-methyl histamine |
| 14 | Asparagine |
| 15 | Lysine |
| 16 | O-acetylcarnitine |
| 17 | Serine |
| 18 | Alanine |
| 19 | Isoleucine |
| 20 | 3-methyl adipic acid |
| 21 | Tyrosine |
| 22 | 3-hydroxy butyric acid |
| 23 | Succinic acid |
| 24 | Glycine |
| 25 | Sarcosine |
| 26 | Histidine |
| 27 | Betaine |
| 28 | Threonine |
| 29 | Taurine |
| 30 | 3-hydroxy isovaleric acid |
| 31 | Glutamine |

The number of metabolites chosen in the Examples below was based on data from a cohort of subjects and describes the preferred embodiment, since the sensitivity and specificity were optimized with this number of metabolites. However, there is evidence that with the removal of some of the metabolites from the model reasonable accuracy is maintained. In addition, the sample size of subjects outlined in the Examples, while reasonable, is still relatively small when compared to some larger studies. It would be anticipated that as the sample size increases and additional data from the urine analysis using mass spectrometry (MS) is amassed to create the predetermined disease state profiles, some of the listed metabolites will not be required for appropriate diagnosis. This is supported by the MS data disclosed herein, where reasonable diagnostic accuracy (R2 0.8 Q2 0.5) can be seen with the use of 14 metabolites (see FIGS. 6 and 7). Using the MS method described below the number of metabolites used for analysis can be decreased to 11. With this number of metabolites each of the subjects remain correctly in their diagnostic grouping, with the exception of one COPD subject.

As such, it is reasonable that the methods described herein could be a diagnostic with as few as 10 of the listed metabolites. In a preferred embodiment this list of 11 metabolites would include 3-Hydroxyisovalerate, Glutamine, Arginine, Lactic acid, Glycolate, Tyrosine, 2-oxoglutarate, Glycine, Histidine, 1-methylhistamine and Taurine.

More specifically, in order to obtain the metabolomic data from a sample from a subject in order to identify a subject profile, a quantitative analysis of more than one metabolite of interest can occur within the clinicians' office or associated lab. This analysis would include two separate runs through a mass spectrometer machine.

By way of general overview, the subject provides a urine sample, which, unlike urine samples collected for other tests, must be saved in such a way as to prevent bacterial growth from occurring, because bacterial growth alters the metabolomics data. One method which has been developed involves cooling and quickly freezing the urine sample within an hour of collection, which preserves the metabolomics data. Repeated thawing and freezing cycles also has been shown to alter the metabolomics data. Therefore, in the preferred embodiment the urine sample is collected from the patient and frozen and not thawed until it is used for NMR or Mass Spectrometry analysis.

It is also contemplated that sodium azide could be used to prevent bacterial growth, however if this method is employed the samples must be stored at minus 80° C.

As disclosed herein and outlined below, it is possible to perform a mass spectrometer analysis for at least 38 metabolites on a single run. In a preferred embodiment 38 metabolites were measured on a single run. Once the metabolomics data has been collected, statistical analysis is performed on the data. In a preferred embodiment, data are analyzed by the PLS-DA models, which can represent various clinical states of asthma or COPD. The physician requesting the analysis can then receive a score for the likelihood that the subject has a predetermined clinical state (e.g. COPD or asthma).

This method can be important in the clinical setting because it can improve the likelihood of obtaining a proper diagnosis of asthma versus COPD, without using invasive techniques, which can lead to more appropriate treatment of the patient and reduce costs within a health care system.

In terms of treatments, after a diagnosis of asthma, treatment may include high dose corticosteroids (inhaled or systemic) and/or new biological therapies that target asthmatic inflammation (e.g. anti-IL5, IgE, or IL13).

These therapies would not be effective in COPD and obtaining a more definitive diagnosis of asthma as opposed to COPD could avoid unnecessary side-effects for those with COPD (e.g. adrenal suppression) and/or unnecessary costs (e.g. biologics are very expensive).

Alternatively, after a diagnosis of COPD, treatment may include anti-muscarinic inhalers, antibiotics, lung surgery (e.g. lobectomy), or lung transplantation.

In order to determine whether there were metabolic differences between asthma and COPD patients, and to create asthma and COPD metabolic models, clinical and urine-based nuclear magnetic resonance spectroscopy (NMR) and mass spectrometry (MS) data can be collected on adults meeting criteria of asthma and COPD before and after an exacerbation and from subjects with stable asthma or COPD. Statistical analysis can be performed on the NMR or MS data to create models of separation providing unique differences in select metabolites between asthma and COPD subjects seen in the Emergency Department and in follow-up after treatment. In some embodiments the statistical analysis that can be performed can be partial least squares discriminant analysis (PLS-DA). Using these select metabolomic profiles, the model can correctly diagnose blinded asthma and COPD subjects with >90% accuracy, showing that metabolomic analysis of human urine samples can be a useful clinical tool to differentiate asthma from COPD.

Without any limitation to the foregoing, the present method is further described by way of the following examples.

Example 1

Patient Characteristics

Asthma or COPD patients with exacerbation: Adults with asthma seen at the time of an exacerbation through either Location 1 (n=110) or Location 2 (n=23) were selected based on one or more of the following: a) increasing asthma symptoms (e.g., cough, wheeze, shortness-of-breath, or chest tightness) requiring assessment and a history of similar episodes; b) bronchodilator response measured by peak expiratory flow (PEF) or significant clinical improvement and/or c) had a previous history of physician-diagnosed asthma. Those from Location 2 also had previously demonstrated >12% reversibility to salbutamol or a positive methacholine challenge test (PC20 less than 8 mg/ml). Adults with COPD seen in the ED at Location 1 (n=38) were selected based on one or more of the following: a) increasing symptoms (e.g., cough, wheeze, shortness-of-breath, or chest tightness) requiring assessment and a history of similar episodes; b) had a previous history of physician-diagnosed COPD. All patients had to present primarily for acute asthma or COPD exacerbation (not a simple prescription refill) and were excluded if they had acute pneumonia, needed immediate resuscitation (status asthmaticus), had cognitive impairment, or had a known immunodeficiency. Some subjects consented to return for a follow-up survey and urine collection. Available clinical data are shown in Table 2.

Asthma or COPD patients stable in an outpatient setting: Adults with asthma (n=58) or COPD (n=24) were recruited in an outpatient setting at Location 1. Asthma diagnosis was based on: a) a previous history of physician-diagnosed asthma; b) previously demonstrated >12% reversibility to salbutamol or a positive methacholine challenge test (PC20 less than 8 mg/ml), c) not currently smoking; and d) having a <10 pack year history of smoking in their past. COPD diagnosis was based on one or more of the following: a) a previous history of physician-diagnosed COPD; b) having a post-bronchodilator FEV1/FVC <70%. Patients were excluded if they were taking systemic corticosteroids or prescription medications for diabetes or hypothyroidism. Available clinical data are shown in Table 2.

Statistical Analysis of Clinical Data

GraphPad Prism™ (V.6) was used for statistical analysis of the clinical data. A non-parametric t-test was used to compare two group experiments. Repeated Measures ANOVA with Bonferroni's Multiple Comparison Test were employed to compare multiple groups. Data are presented as mean±1 standard error (SEM) or median with interquaterile range (IQR). A p value of <0.05 was considered significant.

Urine Sample Collection and Preparation

A urine sample was collected from each patient and promptly placed in a freezer (−20° C.). Within 3 hours of collection, the urine samples were stored in a −80° C. freezer. Urine samples were thawed only once in a biosafety fume hood and a 630 µl aliquot was removed and placed in a 1.5 ml Eppendorf tube followed by the addition of 70 µl of a reference buffer solution.

NMR Spectral and Statistical Analysis

Quantification of 86 metabolites was performed using the Chenomx NMR Suite Professional software package Version 4.6 (Chenomx Inc., Edmonton, AB). The software contains a database of known metabolites with their referenced spectral resonant frequencies or signatures enabling the qualitative and quantitative analysis of metabolites in urine. To account for hydration status of the subjects, metabolites were referenced to creatinine and the values were log transformed. Partial least squares discriminate analysis (PLS-DA) was performed (SIMCA-P 11, Umetrics, USA). This process identifies the metabolites whose concentrations differed significantly between groups of patients. In some embodiments, most metabolites do not differ greatly between groups and including metabolites of low significance can be detrimental to creating an accurate diagnostic model of separation. Metabolites with consistently greater difference in concentration between groups are displayed by the software as a Co-efficient of Variation (COV) Plot and Variables of Importance Plot (VIP). To choose an accurate list of metabolites, metabolites were removed until the model could correctly diagnose blinded samples not part of the model at a satisfactory level. A false positive rate of 5-10% was set as an acceptable limit. The PLS-DA based

TABLE 2

| Characteristics of subjects | | | | | |
|---|---|---|---|---|---|
| | Alberta Asthma model (n = 110) | Alberta COPD model (n = 38) | McMaster Asthma Test Set (n = 23) | Alberta Outpatient Asthma Test Set (n = 58) | Alberta Outpatient COPD Test Set (n = 23) |
| Mean Age (in years) | 32.7 | 69.4 | 49.9 | 33.9 | 59.2 |
| (±SD) | (±11.3) | (±12.2) | (±15.7) | (±13.2) | (±13.1) |
| Female Sex N | 70 | 23 | 14 | 34 | 10 |
| (% of the cohort) | (62%) | (52%) | (61%) | (59%) | (43%) |
| Current smoker N | 32 | 19 | 0 | 0 | 7 |
| (%) | (28.3%) | (43.2%) | | | (32%) |
| Pack-years of smoking Median (IQR) | 5 (2, 8) | 33.3 (25, 43) | unknown | 0 (0, 2.75) | 30 (15, 44) |
| FEV1 (L) Median, (IQR) | unknown | 0.81 (0.58, 1.22) | 1.81 (1.12, 2.30) | 3.31 (2.87, 3.62) | 1.96 (1.42, 2.41) |
| FEV1 (%) Median, (IQR) | unknown | 35.0 (25.0, 50.8) | 66.5 (37.0, 82.0) | 91.5 (81.8, 98.0) | 69.0 (54.0, 77.3) |
| Inhaled Corticosteroid N | 78 | 32 | unknown | 46 | 21 |
| (%) | (68) | (80) | | (85) | (95) | model can then be used to generate a prediction score (0-1) of unclassified, blinded data not part of the model (i.e., scores <0.5 would be predicted to be asthma vs. COPD subjects). The receiver-operator curve (ROC) was generated to evaluate the relationship between the sensitivity and specificity of the prediction score at various cutpoints, and to consider the score's overall function as a predictor.

Baseline Patient Characteristics for the Metabolomic Model of Asthma Versus COPD The COPD populations were both significantly older than the asthma groups, though the asthma group from Location 2 was significantly older than the other asthma cohorts in Location 1. The sex difference among these groups was similar. Subjects having an asthma exacerbation at the Location 1 were not excluded if they currently smoked; however, the number of pack years of smoking was much lower in the asthma group compared to the COPD exacerbation group (a median of 5 pack years compared to 33 respectively). None of the subjects recruited with asthma at Location 2 were current smokers and all had <10 pack years of past smoking history. All the COPD subjects used to create the models of asthma versus COPD in the ED or in follow-up had smoked at one time. Their pack years of smoking were also substantially higher compared to the asthma groups. There were four COPD subjects in the Location 1 COPD outpatient test set that denied ever smoking. That being said, there were also a number of patients with asthma included in the models that were current smokers. Regarding lung function data, FEV1 was significantly lower in the COPD cohort compared to the blinded asthma cohort from Location 2 (p<0.003). Spirometry data were not available from the asthma model subjects from Location 1. Only the Location 2 cohort had skin testing performed; 13 of the 23 subjects (56%) were skin test positive for at least one aeroallergen.

Baseline Patient Characteristics for the Test Set of Outpatient Asthma Versus COPD Adults having a diagnosis of asthma or COPD were recruited for urine sampling in an outpatient setting (Table 2). The COPD population was significantly older than the asthma group. The sex difference between these groups was similar. Patients with asthma were excluded based on smoking history as such they had a lower pack year history of smoking compared to the COPD group. Regarding lung function data, FEV1% predicted and the FEV1/FVC were both significantly lower in the COPD cohort compared to the blinded asthma cohort from Location 2 (p<0.0001 each).

Urine Metabolomic Profiling can Differentiate Asthma Versus COPD Exacerbation

The metabolites of asthma and COPD patients were compared. Most of the metabolites excreted in the urine did not differ greatly between groups, and adding metabolites of low importance rendered the PLS-DA based model less accurate. To remove irrelevant metabolites, urine samples from 19 patients with asthma were randomly withheld to be used as a test set. The model used 91 subjects with asthma and 38 with COPD. Using the test set, metabolites that allowed the model to correctly classify these blinded asthma patients with 95% accuracy were removed (18 of 19 with a blinded PLS-DA prediction score >0.5). The final list of remaining metabolites used one component consisting of 22 metabolites in the VIP list giving an R2=0.72, Q2=0.69.

Referring now to FIG. 1, an embodiment of a metabolomic model of exacerbation of asthma versus COPD in the ED is depicted. Urine metabolite levels were measured in subjects in the ED with either an exacerbation of asthma or COPD. Using a blind test set, PLS-DA analysis (SIMCA P-11) of these metabolites created a model of separation (R2=0.72, Q2=0.69). Illustrated are: A. the Variables of Importance plot ranking the metabolites according to their significance in the model; B. scaled and centered metabolite differences between groups shown as the Coefficients of Variation plot. Metabolites that were higher in COPD than Asthma subjects are shown with bars rising above zero, while those higher in Asthma than COPD are going below; C. the PLS-DA prediction scores for each subject with error bars representing medians and interquartile ranges. The PLS-DA algorithm separates groups of data based on a score of 0-1; in this case a value above 0.5 indicates the subject has asthma while below 0.5 indicates COPD.

The importance of the metabolites used for separation of these two groups is shown as a VIP Plot (FIG. 1A). The differences in concentration of these metabolites between groups are shown as the COV Plot (FIG. 1B). Metabolites that were higher in COPD than asthma subjects are shown with bars rising above zero, while those higher in asthma than COPD are going below. Graphic presentation of the quality of separation between groups in the model is shown by their respective PLS-DA scores (FIG. 1C). The final metabolites chosen and their concentrations are shown in Table 3.

TABLE 3

The concentration of each metabolite for each subject group is shown as the median and interquartile range (IQR) in mmol of metabolite/mmol creatinine (except for creatinine for which actual values are shown (mmol)). The metabolites used to discriminate the different groups of subjects are labeled as: (α) required for separation of COPD vs asthma during exacerbation: (β) required for separation of COPD vs asthma in follow-up.

|  | Median | IQR | | Median | IQR | |
| --- | --- | --- | --- | --- | --- | --- |
|  | COPD in ED | | | Asthma ED | | |
| 1-Methylnicotinamide (β) | 0.0034 | 0.0010 | 0.0055 | 0.0024 | 0.0010 | 0.0037 |
| 3-Hydroxyisovalerate (α, β) | 0.0050 | 0.0026 | 0.0088 | 0.0066 | 0.0047 | 0.0097 |
| Arginine (α, β) | 0.0070 | 0.0065 | 0.0245 | 0.0189 | 0.0134 | 0.0237 |
| Ascorbate (α) | 0.0005 | 0.0005 | 0.0302 | 0.0005 | 0.0005 | 0.0005 |
| Betaine (α, β) | 0.0138 | 0.0056 | 0.0278 | 0.0071 | 0.0050 | 0.0105 |
| Choline (α, β) | 0.0029 | 0.0006 | 0.0047 | 0.0006 | 0.0006 | 0.0025 |
| Citrate (α) | 0.1986 | 0.0819 | 0.3327 | 0.2443 | 0.1744 | 0.3673 |
| Creatinine (α) | 6671 | 2394 | 9324 | 11252 | 6094 | 18286 |
| Dimethylamine (α, β) | 0.0457 | 0.0395 | 0.0525 | 0.0340 | 0.0300 | 0.0391 |
| Glucose (α, β) | 0.0711 | 0.0337 | 1.6860 | 0.0334 | 0.0218 | 0.0473 |
| Glutamine (α, β) | 0.0286 | 0.0158 | 0.0466 | 0.0392 | 0.0319 | 0.0539 |

TABLE 3-continued

The concentration of each metabolite for each subject group is shown as the median and interquartile range (IQR) in mmol of metabolite/mmol creatinine (except for creatinine for which actual values are shown (mmol)). The metabolites used to discriminate the different groups of subjects are labeled as: (α) required for separation of COPD vs asthma during exacerbation: (β) required for separation of COPD vs asthma in follow-up.

|  | Median | IQR |  | Median | IQR |  |
|---|---|---|---|---|---|---|
| Glycine (β) | 0.0952 | 0.0486 | 0.1594 | 0.1160 | 0.0640 | 0.2006 |
| Glycolate (α) | 0.0258 | 0.0176 | 0.0413 | 0.0366 | 0.0258 | 0.0552 |
| Guanidoacetate (α, β) | 0.0091 | 0.0020 | 0.0186 | 0.0166 | 0.0103 | 0.0255 |
| Histidine (α, β) | 0.0300 | 0.0139 | 0.0484 | 0.0353 | 0.0202 | 0.0549 |
| Hypoxanthine (α, β) | 0.0083 | 0.0035 | 0.0131 | 0.0056 | 0.0025 | 0.0091 |
| Isoleucine (α) | 0.0017 | 0.0003 | 0.0032 | 0.0009 | 0.0003 | 0.0016 |
| Methanol (α) | 0.0029 | 0.0015 | 0.0070 | 0.0016 | 0.0011 | 0.0036 |
| Pantothenate (α) | 0.0050 | 0.0027 | 0.0075 | 0.0030 | 0.0017 | 0.0045 |
| Phe-Derivative (α, β) | 0.1044 | 0.0754 | 0.1392 | 0.0481 | 0.0279 | 0.0726 |
| Succinate (β) | 0.0056 | 0.0037 | 0.0112 | 0.0065 | 0.0030 | 0.0117 |
| Taurine (α, β) | 0.1148 | 0.0314 | 0.2133 | 0.0184 | 0.0051 | 0.0517 |
| Uracil (α, β) | 0.0010 | 0.0010 | 0.0018 | 0.0028 | 0.0010 | 0.0046 |
| Urea (α) | 26.73 | 17.38 | 36.81 | 19.58 | 14.42 | 27.06 |
| Xylose (α) | 0.0239 | 0.0020 | 0.0487 | 0.0080 | 0.0020 | 0.0163 |
| | COPD ED-followup | | | Asthma ED-followup | | |
| 1-Methylnicotinamide (β) | 0.0035 | 0.0010 | 0.0071 | 0.0016 | 0.0010 | 0.0034 |
| 3-Hydroxyisovalerate (α, β) | 0.0034 | 0.0017 | 0.0044 | 0.0063 | 0.0051 | 0.0082 |
| Arginine (α, β) | 0.0082 | 0.0070 | 0.0234 | 0.0190 | 0.0146 | 0.0240 |
| Ascorbate (α) | 0.0005 | 0.0005 | 0.0131 | 0.0005 | 0.0005 | 0.0005 |
| Betaine (α, β) | 0.0095 | 0.0049 | 0.0173 | 0.0057 | 0.0034 | 0.0088 |
| Choline (α, β) | 0.0024 | 0.0011 | 0.0041 | 0.0013 | 0.0006 | 0.0024 |
| Citrate (α) | 0.2752 | 0.1387 | 0.4160 | 0.2417 | 0.1534 | 0.4114 |
| Creatinine (α) | 5213 | 2910 | 7474 | 10426 | 5928 | 18413 |
| Dimethylamine (α, β) | 0.0419 | 0.0369 | 0.0464 | 0.0330 | 0.0289 | 0.0375 |
| Glucose (α, β) | 0.0375 | 0.0291 | 0.0631 | 0.0271 | 0.0223 | 0.0354 |
| Glutamine (α, β) | 0.0196 | 0.0167 | 0.0309 | 0.0446 | 0.0298 | 0.0548 |
| Glycine (β) | 0.0759 | 0.0497 | 0.1113 | 0.1041 | 0.0672 | 0.2057 |
| Glycolate (α) | 0.0210 | 0.0118 | 0.0321 | 0.0347 | 0.0235 | 0.0498 |
| Guanidoacetate (α, β) | 0.0143 | 0.0104 | 0.0244 | 0.0166 | 0.0092 | 0.0270 |
| Histidine (α, β) | 0.0177 | 0.0112 | 0.0257 | 0.0290 | 0.0117 | 0.0441 |
| Hypoxanthine (α, β) | 0.0060 | 0.0009 | 0.0076 | 0.0036 | 0.0009 | 0.0070 |
| Isoleucine (α) | 0.0013 | 0.0003 | 0.0020 | 0.0006 | 0.0003 | 0.0015 |
| Methanol (α) | 0.0054 | 0.0024 | 0.0072 | 0.0021 | 0.0010 | 0.0039 |
| Pantothenate (α) | 0.0024 | 0.0016 | 0.0081 | 0.0026 | 0.0018 | 0.0035 |
| Phe-Derivative (α, β) | 0.0948 | 0.0722 | 0.1442 | 0.0538 | 0.0290 | 0.0942 |
| Succinate (β) | 0.0060 | 0.0027 | 0.0111 | 0.0067 | 0.0042 | 0.0151 |
| Taurine (α, β) | 0.0568 | 0.0219 | 0.1045 | 0.0078 | 0.0042 | 0.0141 |
| Uracil (α, β) | 0.0010 | 0.0010 | 0.0039 | 0.0029 | 0.0010 | 0.0055 |
| Urea (α) | 27.56 | 19.15 | 39.22 | 19.94 | 14.34 | 28.37 |
| Xylose (α) | 0.0020 | 0.0020 | 0.0151 | 0.0072 | 0.0020 | 0.0142 |

Validity Assessment (Asthma Vs COPD During Exacerbation)

To validate the proposed metabolomic model and its applicability as a diagnostic tool for asthma in the ED setting, the concentrations of metabolites from adults (n=23) with asthma exacerbation from Location 2 were entered. The urine metabolite values for these patients were entered into the PLS-DA model without a diagnosis, thus the computer was blinded for the PLS-DA derived model of asthma versus COPD. The individual PLS-DA prediction scores are shown in FIG. 1C. A threshold PLS-DA score of >0.5 was used to designate asthma. The model was able to correctly diagnose the blinded asthma samples in 20 of 23 samples (87% accuracy).

Urine Metabolomic Profiling can Differentiate Asthma Versus COPD in Follow-Up after an Exacerbation To determine if this metabolomic approach could be used to differentiate asthma and COPD in the outpatient setting, urine samples were studied from the asthma or COPD subjects 1-2 weeks post-exacerbation (Table 2). This follow-up data were also obtained to determine a measure of reproducibility for this metabolomic approach (i.e., if these data were simply dependent on confounders such as time of day or diet). 61 asthma and 23 COPD subjects were used to create a follow-up model. The same returning asthma subjects (now n=16) were withheld as a test set to remove metabolites of low importance.

Figure 2:
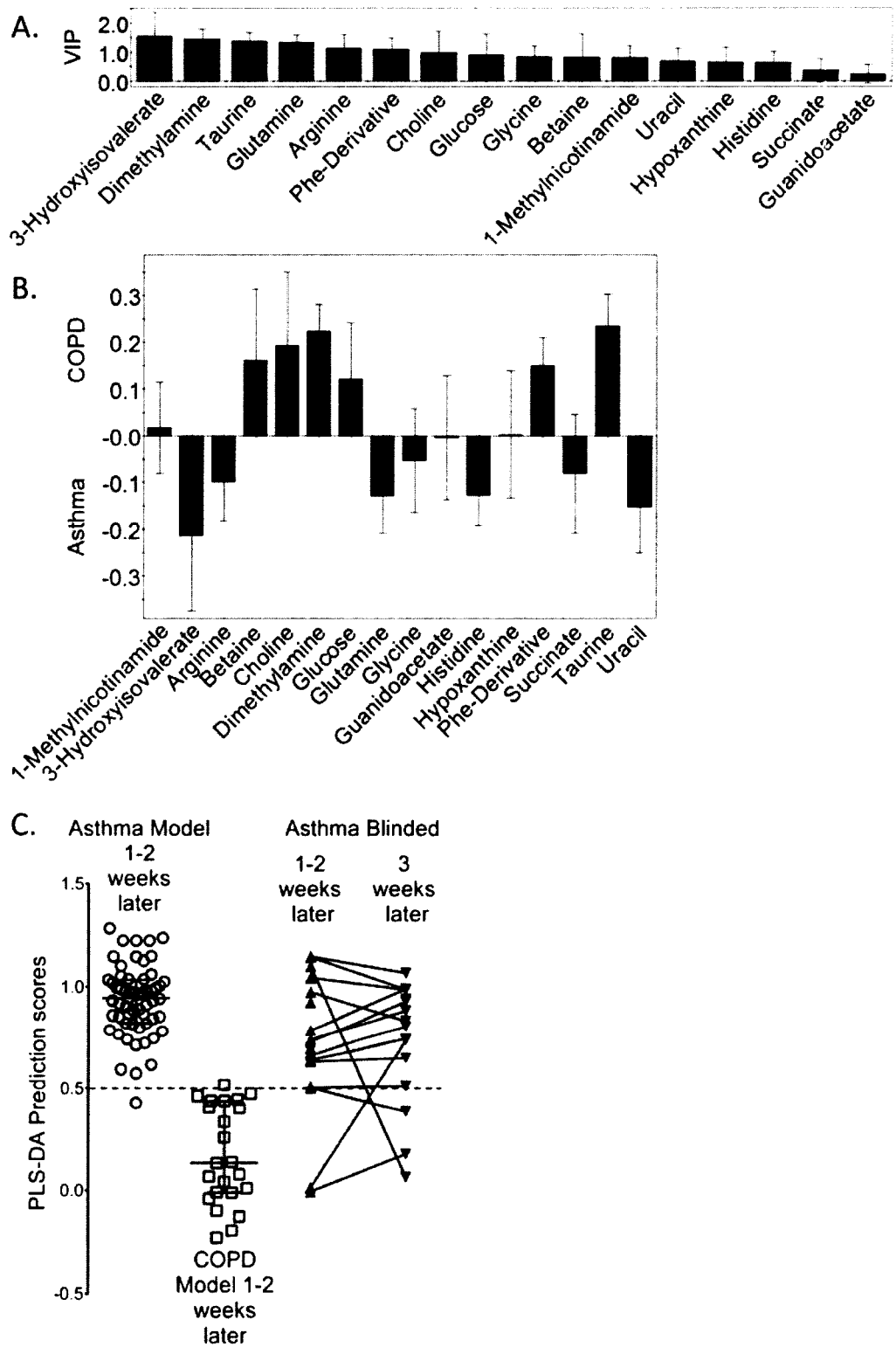
FIGS. 2A-2C depict an embodiment of a metabolomic model of subjects in follow-up post-exacerbation of asthma versus COPD.

Referring now to FIG. 2, an embodiment of a metabolomic model of subjects in follow-up post-exacerbation of asthma versus COPD is depicted. Urine metabolite levels can be measured from subjects in follow-up from an ED visit for either asthma or COPD. Using a blind test set, PLS-DA analysis (SIMCA P-11) on these metabolite levels created a model of separation ($R2=0.78$, $Q2=0.70$). Illustrated are: A. the Variables of Importance plot ranking the metabolites according to their significance in the model; B. scaled and centered metabolite differences between groups shown as the Coefficients of Variation plot; C. the PLS-DA prediction scores for each subject with error bars representing medians and interquartile ranges. The PLS-DA algorithm separates groups of data based on a score of 0-1; in this case a value above 0.5 indicates the subject has asthma while below 0.5 indicates COPD.

The metabolomic model can correctly classify a blinded asthma test set with 94% accuracy ([16/17]). The final list of metabolites used to separate post-exacerbation asthma versus COPD used two components consisting of 16 metabolites in the VIP list producing an R2=0.76, Q2=0.70 (VIP, FIG. 2A). Most of the metabolites used for this follow-up visit model were the same as those used for the first visit model and the direction of difference of each metabolite between groups (i.e., greater or lesser) was the same (see COV plot 2B). Graphic presentation of the quality of separation between groups in the model is shown by their respective PLS-DA scores (FIG. 2C). The final list of metabolites chosen and their concentrations are shown in Table 3.

Validity Assessment of this Model Studying Post-Exacerbation

To validate the metabolomic model of asthma versus COPD post-exacerbation, the concentrations of metabolites from Location 2 (n=21) were entered. These urine metabolite values were entered blindly for the PLS-DA model to predict a diagnosis. The individual PLS-DA prediction scores are shown in FIG. 2C with error bars representing medians and interquartile ranges. The model was able to correctly diagnose 19 of 21 blinded asthma samples (90% accuracy).

Validity Assessment of this Model Studying Stable Asthma Versus COPD in an Outpatient Setting To better validate the proposed metabolomic model of asthma versus COPD, the concentrations of metabolites from another cohort of adults with asthma or COPD were entered. These subjects were recruited in an outpatient setting and not specifically post-exacerbation. This is to show if the model would still perceive similar metabolomic differences in what should be a somewhat healthier group not recently recovering from an exacerbation.

Figure 3:
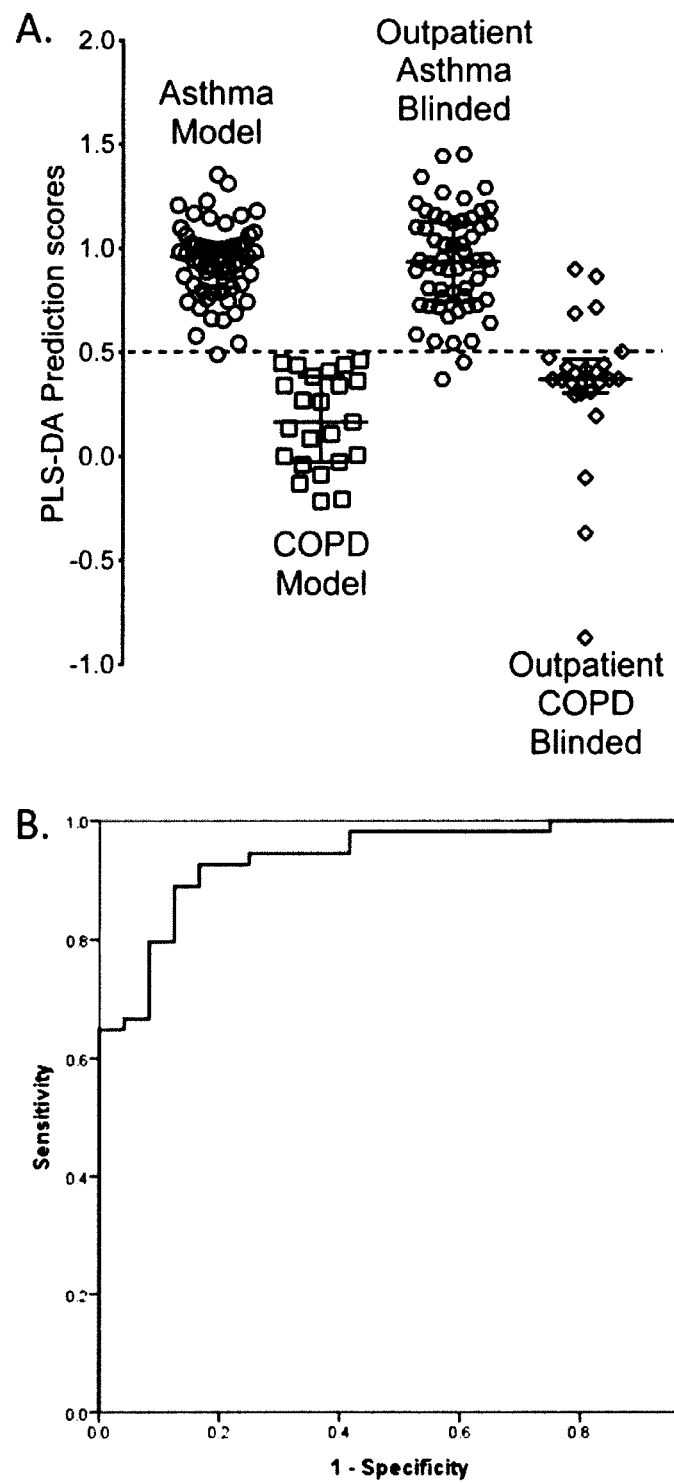
FIGS. 3A-3B depict an embodiment of a metabolomic model correctly predicting asthma versus COPD in blinded outpatients.
Figure 4A:
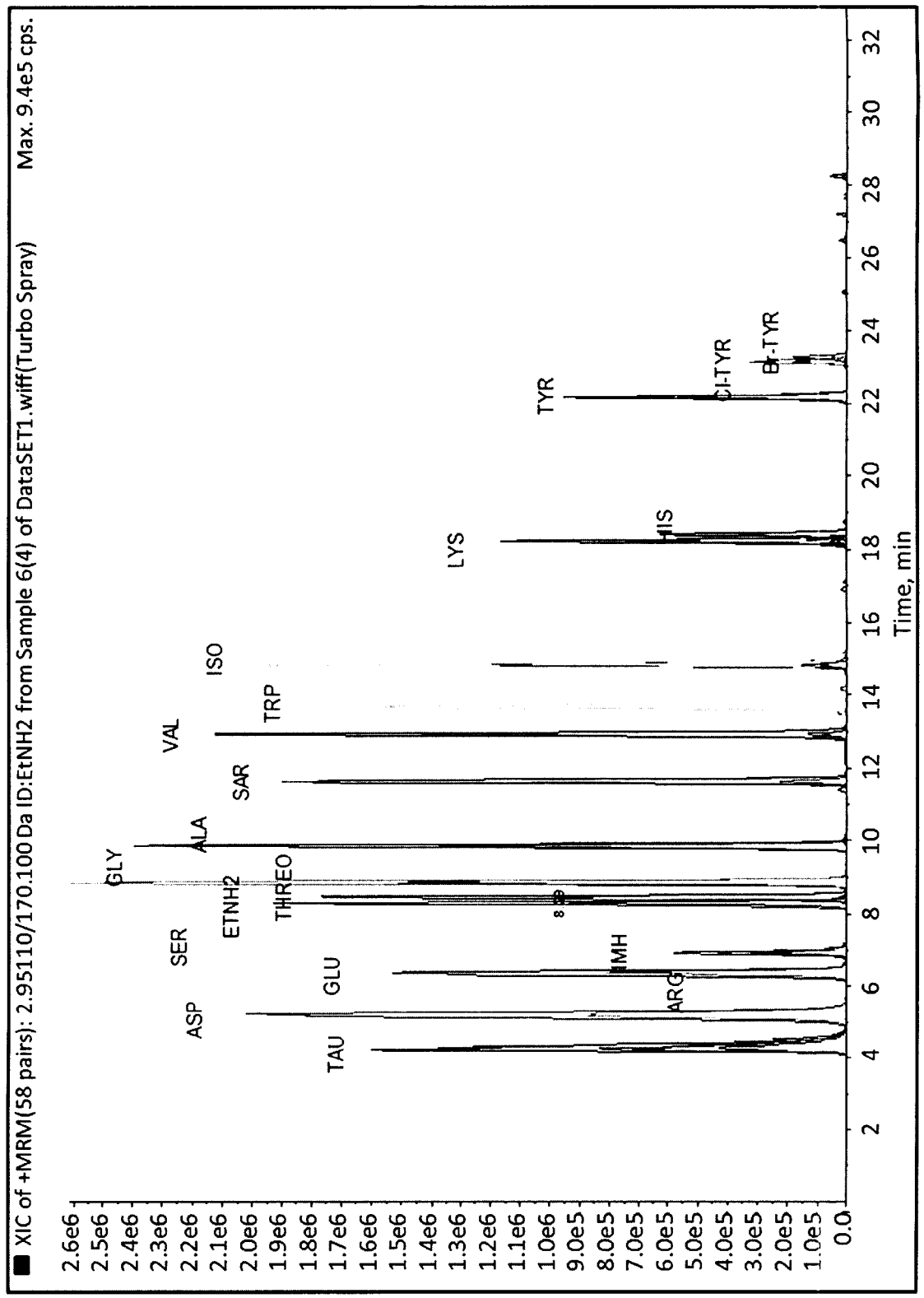
FIG. 4 depicts representative LC-MS/MS spectra data of phenol or amine functional groups tested for a) standard solution; b) urine of asthma patient; and c) urine of COPD patient.
Figure 4B:
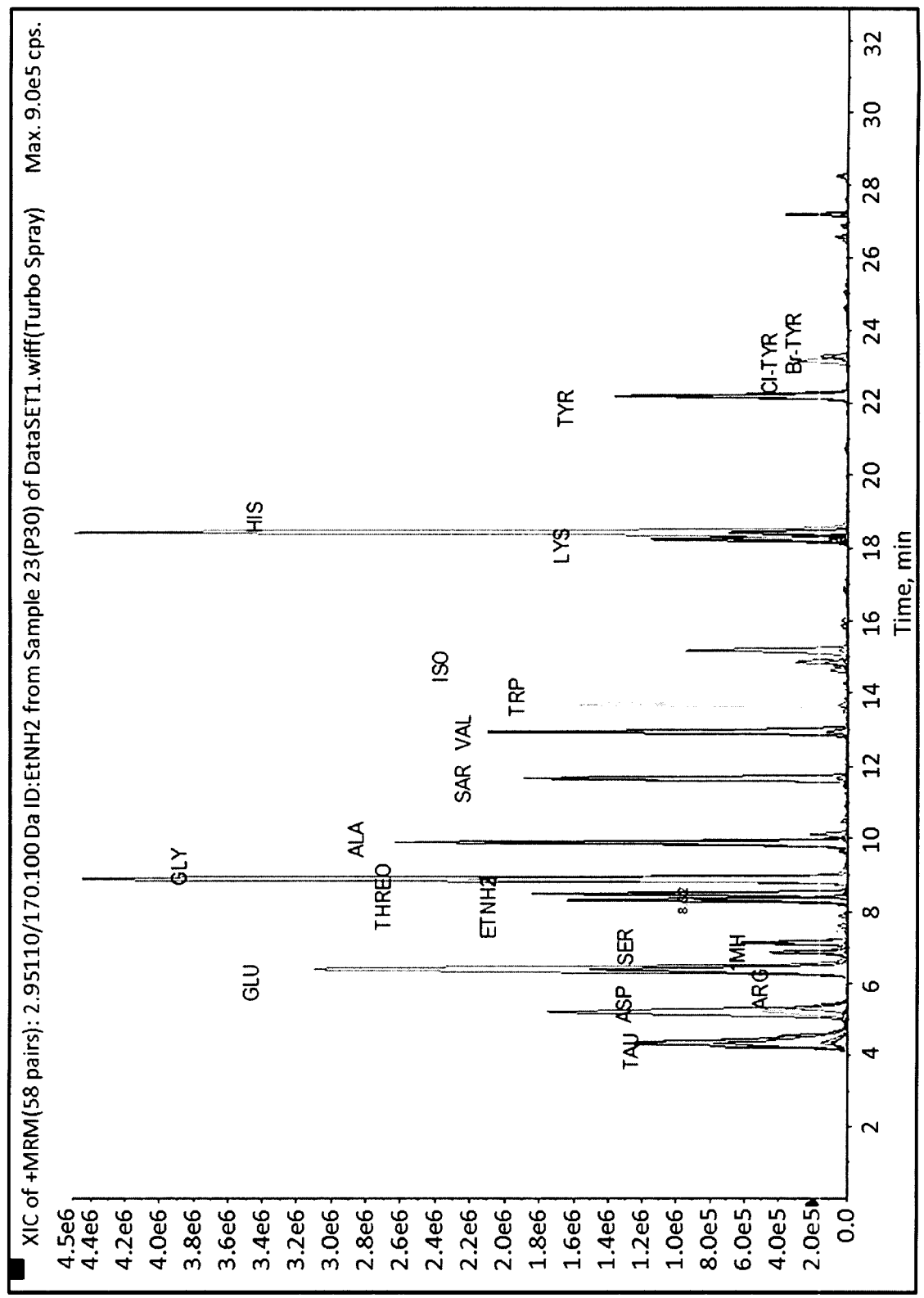
Figure 4C:
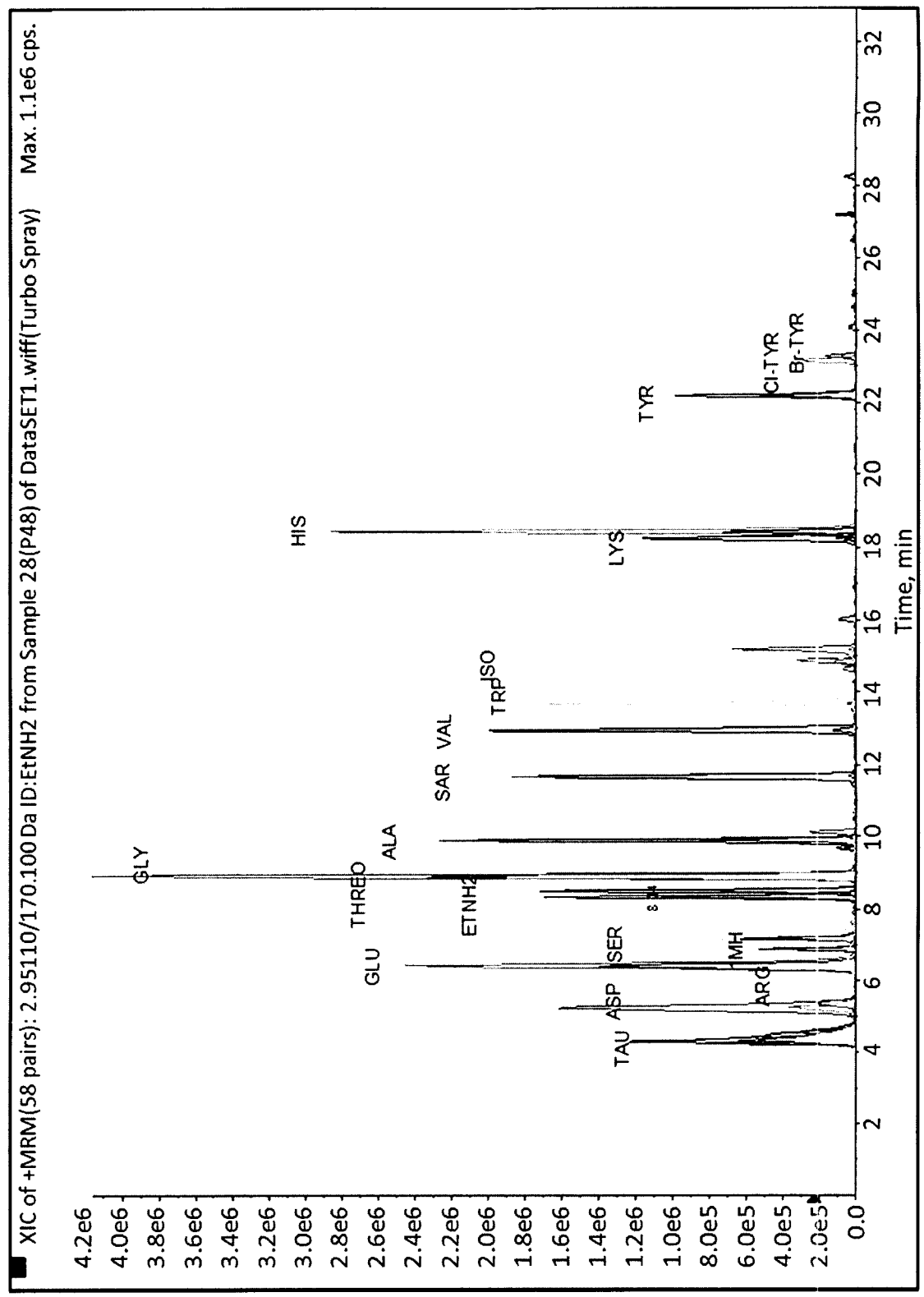
Figure 5A:
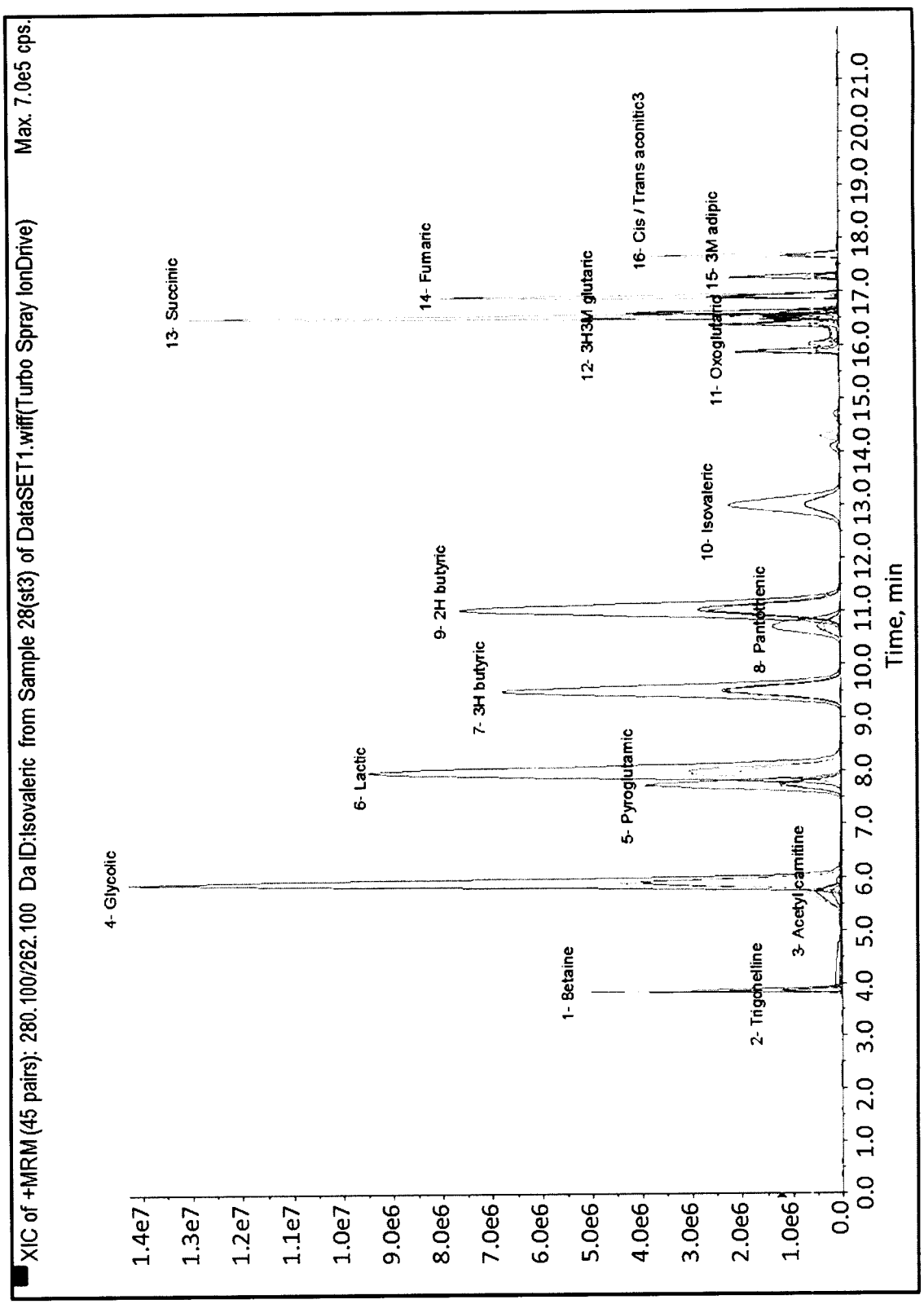
FIG. 5 depicts representative LC-MS/MS spectra data of carboxylic acid functional groups tested for a) standard solution; b) urine of asthma patient; and c) urine of COPD patient.
Figure 5B:
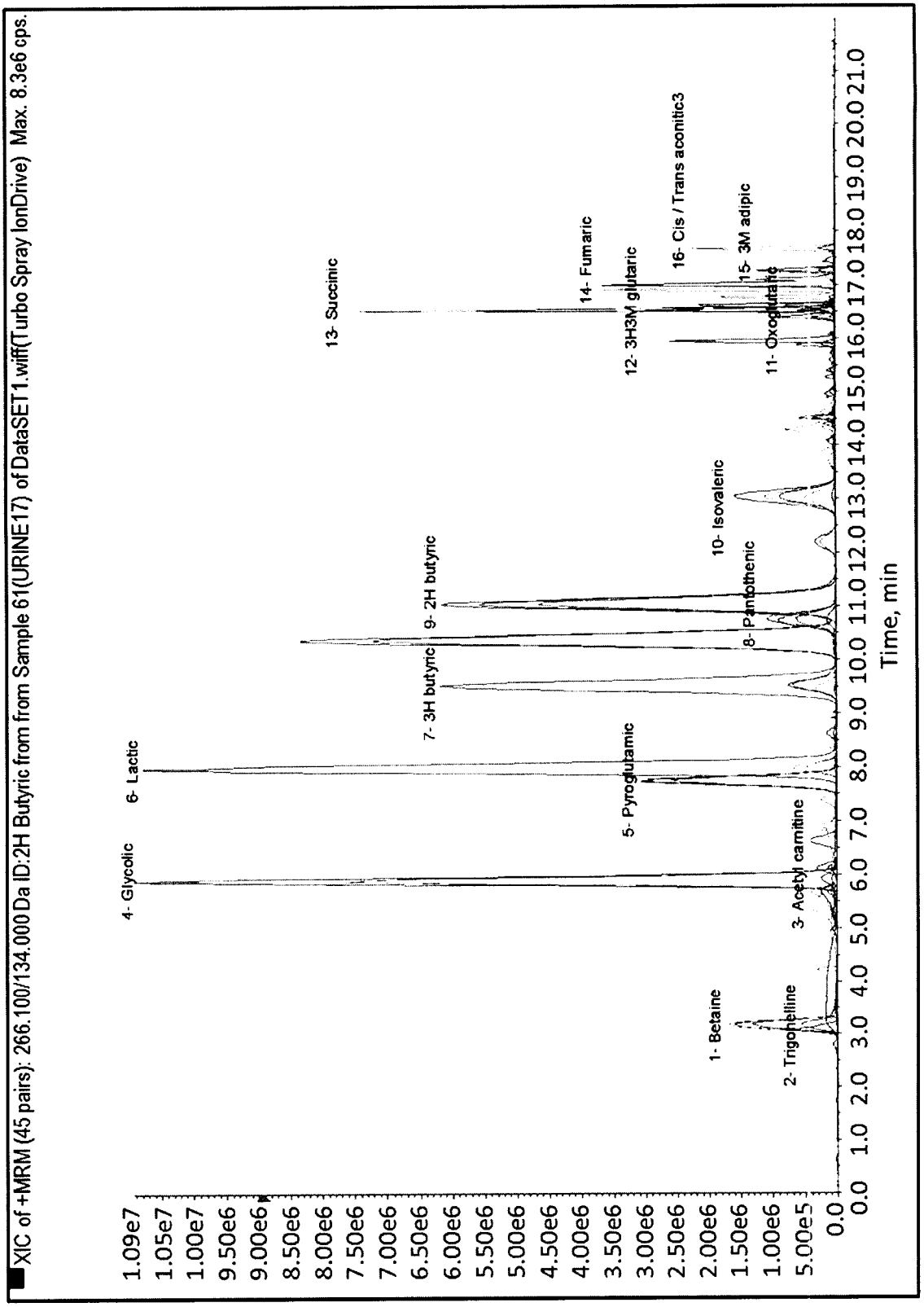
Figure 5C:
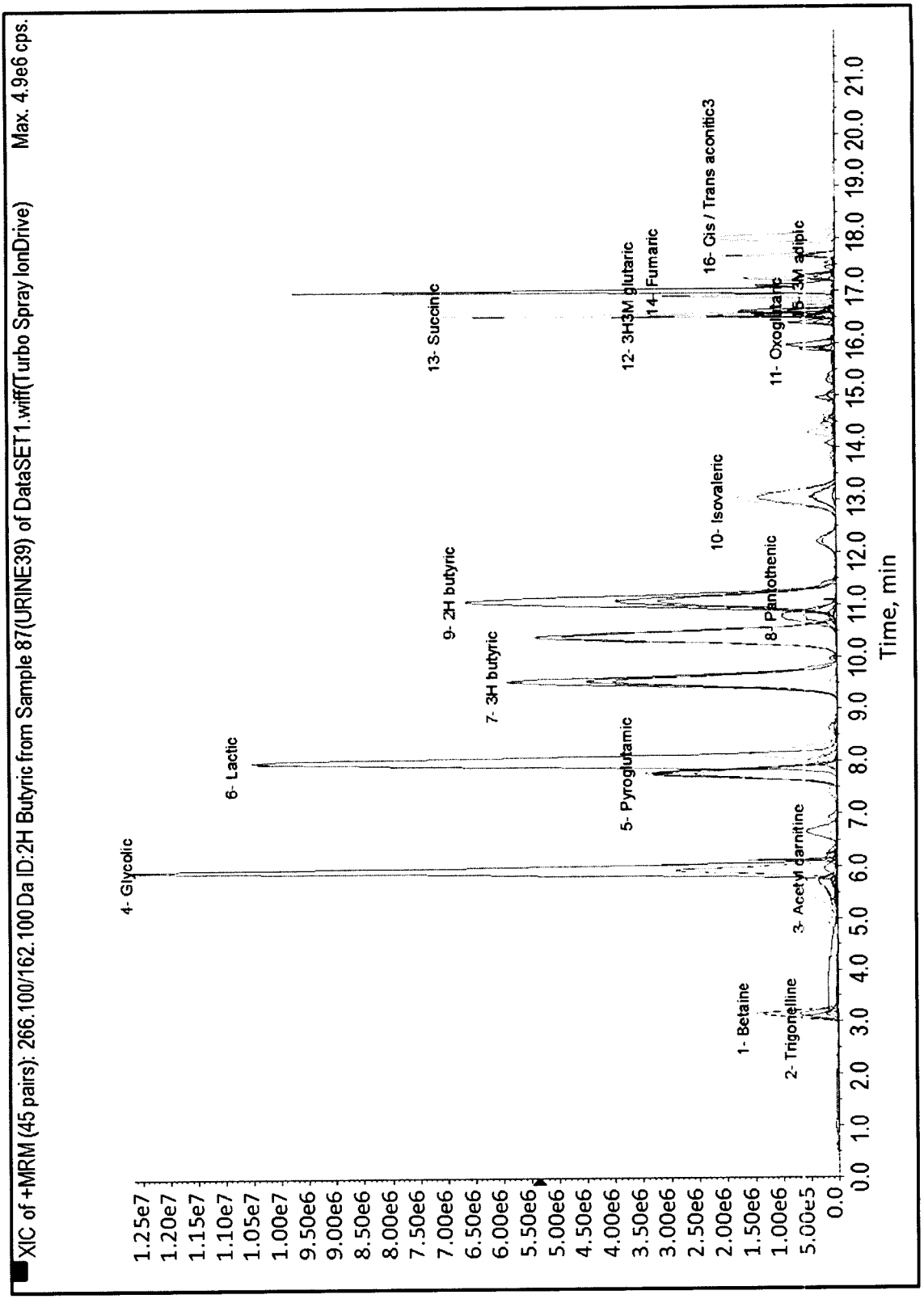

Referring now to FIG. 3, an embodiment of a metabolomic model correctly predicting asthma versus COPD in blinded outpatients is depicted. To further determine diagnostic accuracy, the metabolomic model of asthma versus COPD post-exacerbation was used to study new subjects with asthma or COPD in an outpatient setting. Illustrated are: A. the PLS-DA prediction scores for each subject with error bars representing medians and interquartile ranges. The PLS-DA algorithm separates groups of data based on a score of 0-1; in this case a value above 0.5 indicates the subject has asthma while below 0.5 indicates CORD; B. Receiver-operator curve for the prediction of asthma vs COPD. Area under the curve=0.937.

The individual PLS-DA prediction scores are shown in FIG. 3A with error bars representing medians and interquartile ranges. In some embodiments, the model can have a sensitivity of 92.6% (95% CI=82.1, 97.9) and a specificity of 79.2% (95% CI=57.8, 92.9). The positive predictive value (PPV) for asthma (if prediction score >0.5) was 90.9% (95% CI=80.0, 97.0*) and the negative predictive value (NPV), indicating COPD rather than asthma, (prediction score ≤0.5) was 82.6% (95% CI=61.2, 95.0). The ROC curve is shown (FIG. 3B, AUC=0.937).

In current practices, some patients with asthma can be difficult to differentiate from COPD if they are current smokers. Smokers were not excluded from the asthma cohort in the ED, since patients with asthma still continue to smoke. There were 32 asthma patients (28.3%) included in the models that were current smokers. Despite this, the models saw the nonsmoking asthma patients in the test sets correctly as asthma. As such, smoking was not the major factor in the metabolomic differentiation of asthma and COPD of the present disclosure.

Even with optimal clinical phenotyping using current methods, some asthma may mimic the lung function changes typically seen in COPD. Standard clinical criteria, cigarette consumption limits, and FEV1/FVC ratios were used in an effort to accurately classify the groups. Despite this, some of the follow-up asthma exacerbation subjects had fixed obstruction even three weeks post-exacerbation. They were left in the category of asthma based on prior spirometry showing reversibility or hyperresponsiveness. The fact that the metabolome model still identifies them as asthma despite this fixed obstruction makes the current results even more compelling. This would suggest that a subject may have a unique metabolomic phenotype that transcends this physiologic presentation of fixed obstruction. This approach might also help to define COPD and asthma overlap syndromes.

While this study was not designed to mechanistically confirm specific metabolic pathways, there is a sound line of reasoning from which the results of the methods and uses herein can be inferred from a factual basis.

Example 3

Procedure for Derivatization Using Dansyl Chloride

This process was used in this example to quantify 19 metabolites containing phenol or amine functional groups, however, it may be used to quantify any number of metabolites with these functional groups.

Sample Preparation

The initial stock solution contained metabolites with concentrations ranging from 12.5-160 ng/ml. The $^{12}$C-derivatized stock solution is prepared by mixing 50 µl aliquots of the standard working solution with 30 µl bicarbonate/carbonate buffer (pH 9.4, 0.5 M) and 40 µl $^{12}$C-DNS-CI (10.125 mg/mL in Acetonitrile (ACN)). The mixture is vortexed for 10 sec, spun down and placed in a thermostatically controlled water bath at 60° C. for 30 min. Excess DNS-CI is quenched via the addition of 10 µl 0.25 M NaOH with further heating at 60° C. for 10 min. Fifty µl of 425 mM formic acid (FA) in 50% ACN is added to acidify the medium and the volume is completed to 200 µl with 50% ACN. For the preparation of $^{13}$C-Internal standards ($^{13}$C-IS), the aforementioned protocol is followed with the exception of the use of $^{13}$C-DNS-CI for derivatization. The reaction mixture is finally completed to 250 µl with 50% ACN.

Calibration standards and quality control samples are prepared by spiking proper volumes from $^{12}$C derivatized stock solution into 50 µl of blank surrogate matrix spiked with 10 µl $^{13}$C-IS. The volumes are completed to 100 µl with 50% ACN before being transferred to HPLC vials for analysis.

Urine Sample Preparation

Individual urine samples are two-fold diluted with ACN, vortexed and centrifuged at 13,000 rpm for 10 min. Fifty µl from the supernatant are mixed with 30 µl bicarbonate/carbonate buffer (0.5 M, pH 9.4) and 40 µl $^{12}$C-DNS-CI (10.125 mg/ml). The mixture is vortexed, spun down and placed in a 60° C. thermostatically controlled water bath for 30 min. Ten µl 0.25 M NaOH are added and the mixture is placed in the water bath for an additional 10 min period. The mixture is then acidified with 50 µl 425 mM FA in 50% ACN and the volume is completed to 200 µl with 50% ACN. Fifty microliters of this reaction mixture is spiked with 10 µl $^{13}$C-IS and the volume is completed to 100 µl with 50% ACN before being transferred to an HPLC vial for analysis. For highly abundant metabolites (e.g. glycine, alanine, histidine and glutamine), derivatized urine samples are appropriately diluted with blank surrogate matrix to a volume of 50 μl. The solution is spiked with 10 μl 1302-IS and the volume is completed to 100 μl with 50% ACN.

Blank surrogate matrix is prepared from a pooled urine sample collected from 61 subjects. Derivatization reaction for blank surrogate matrix is processed in the same manner as patient samples with the exception of the use of ACN in place of the derivatizing reagent. Blank surrogate matrix is used as a diluting medium in the preparation of calibration standards and quality control samples. It is also used for diluting patient samples whenever needed.

LC-MS/MS Analysis

Liquid chromatography was performed on a 1200 Agilent HPLC system (Mississauga, ON, Canada) interfaced to an AB Sciex 4000 API QTRAP instrument (AB Sciex, Concord, ON, Canada). Five microliter sample aliquots are injected into the system using a 1200 Agilent autosampler set at 4° C. Chromatographic separation is achieved on a Kinetex C18 Column (100 mm×2.1 mm, 5 μm ID, 100 Å pore size, phenominex, Canada), maintained at 22° C. A binary gradient mobile phase system flowing at 0.25 ml/min is employed using (A) 0.1% formic acid in 5% acetonitrile (ACN) and (B) 0.1% formic acid in ACN. Elution conditions are optimized as follows: t=0 min; 90% A, t=6 min; 70% A, t=19 min; 35% A, t=23 min; 1% A, t=24 min; 1% A, t=24.1 min; 90% A, t=33 min; 90% A.

Quantification is achieved in the MRM scan mode using electrospray ionization in the positive ion mode. The monitored precursor ion →product ion transitions for each $^{12}C$-analyte (dansyl derivatized metabolite), are m/z [M+1-1]+ →m/z 170.10, with the exception of sarcosine that is monitored at m/z [M+1-1]+→m/z 157.10, while the analogues $^{13}C$-internal standards (IS) are monitored at m/z [M+1-1]+→m/z 172.10. A qualifier diagnostic fragment ion is also monitored for each $^{12}C$-analyte to confirm its identity. The Turbo spray ion source temperature is set at 550° C. and the ion spray voltage is at 5.5 kV. Curtain gas (CUR) is set at 30, collision gas (CAD) at 6, nebulizer gas (GS1) at 50 and heater gas (GS2) at 50. The entrance potential (EP) and collision exit potential (CXP) for all transitions are fixed at 10 and 12, respectively. The collision energy (CE) and declustering potential (DP) are optimized for each 12C2-analyte individually. The dwell time is 20 msec for each transition at unit resolution with 1.4504 sec cycle time and 5.007 msec pause between mass ranges. Data processing is achieved on Analyst 1.6 software (Applied biosystems).

Example 4

Procedure for Derivatization Using DmPA

This process was used in this example to quantify 17 metabolites containing carboxylic acid functional groups, however it may be used to quantify any number of metabolites with this functional group.

Sample Preparation

For $^{12}C$-DmPA labeling, a 100 μL of a standard or urine sample is mixed with a 100 μL of TEA (20 μL/mL in ACN). The mixture is vortexed and spun down. Then a 100 μL of $^{12}C$-DmPA (30 mg/mL in ACN) is added, vortexed, and spun down. The resulting mixture is heated in a water bath at 85.0 for 30 minutes. After 30 minutes, the derivatized solution is cooled down to room temperature and diluted by mixing 300 μL of this solution with 300 μL of formic acid solution (20 μL/mL in water). Then, 60 μL of the latter solution is mixed with solvent mix I (for calibration curve samples) or solvent mix II (for the urine samples). The solvent mix I is prepared by mixing 120 μL of diluted urine sample (outlined below) with 80 μL of internal standard solution ($^{13}C$-DmPA standard solution). For the solvent mix II, the diluted urine sample is replaced with 80% ACN. The addition of the formic acid solution and the solvent mixtures (I or II) to the derivatized solution is important for the following reasons: i) terminate the derivatization reaction, ii) enhance the chromatographic peak shape, iii) provide the internal standard, and iv) compensate for the matrix effect of urine. The formic acid terminates the derivatization reaction by changing the medium pH into acidic. The water enhances the peak shape in the LC-MS chromatograms by increasing the water content in the injected samples. The diluted urine sample in solvent mix I compensates the matrix effect of the urine in the calibration curve samples. Finally, all samples are subjected to LC-MS/MS analysis.

For $^{13}C$-DmPA labeling, a 100 μL of a standard solution is mixed with a 100 μL of TEA (20 μL/mL in ACN). The mixture is vortexed and spun down. Then a 100 μL of $^{13}C$-DmPA (30 mg/mL in ACN) is added, vortexed, and spun down. The resulting mixture is heated in a water bath at 85.0 for 30 minutes. The resulting solution will be used as an internal standard solution.

Urine Sample Preparation

For the analysis, the urine samples are thawed only once and centrifuged at 14000 rpm for 10 minutes. Then the urine supernatant is 1:4 diluted with ACN and vortexed to be ready for 12C2-DmPA labeling (referred as the diluted urine sample or surrogate urine).

LC-MS/MS Analysis

ESI-MS/MS analysis of the 17 organic acid standards is conducted on the AB SCIEX 6500 QTRAP® instrument, which is a hybrid triple quadrupole-linear ion trap (QqLIT) mass spectrometer. The MS/MS analysis is performed in the positive ion mode with an ionspray voltage of 5500 V, temperature at 550° C., a declustering potential of 60 V, and collision energy of 20-40 V using nitrogen as a collision gas. All parameters are optimized to ensure the formation of the product ions while maintaining the presence of the precursor ion. In the LC/multiple reaction monitoring (MRM)-MS, two selective transitions are chosen for each compound for identification and quantification. The liquid chromatography is performed on the Agilent 1290 Series UPLC System using a Kinetex C18 column (5 μm×50 mm, 2.1 ID) and a gradient system of two solvents. Solvent A consists of 5 mM ammonium formate, 5% ACN, and 0.1% formic acid. Solvent B consists of 60% ACN, 40% methanol, and 0.1% formic acid. The gradient system started with 95% of solvent A and gradually decreased to 80% over 3 minutes then decreased to 75% over 9 min, followed by another decrease to 20% over 5 min. At the minute 17 of the run time, solvent A started to increase from 20% to 95% over 3 minutes. Finally, solvent A continued at 95% for 10 minutes to equilibrate the column for the next injection. Flow rate is set at 0.25 mL/min and sample injection at 5 μL. The autosampler is set at 4° C. and the column is maintained at 20° C.

With regards to normalization of hydration status and validation, for both Examples 3 and 4 creatinine is used for data normalization to the hydration status of the subject. It is determined using the QuantiChrom™ Creatinine Assay kit (BioAssay Systems, Hayward, Calif. 94545, U.S.A). The quantified metabolites are each normalized to the respective creatinine value in each urine sample. As well, each method was fully validated according to the FDA in terms of precision, accuracy, selectivity, carry over, linear range, dilution integrity, stability and matrix effects.

Example 5

Figure 6:
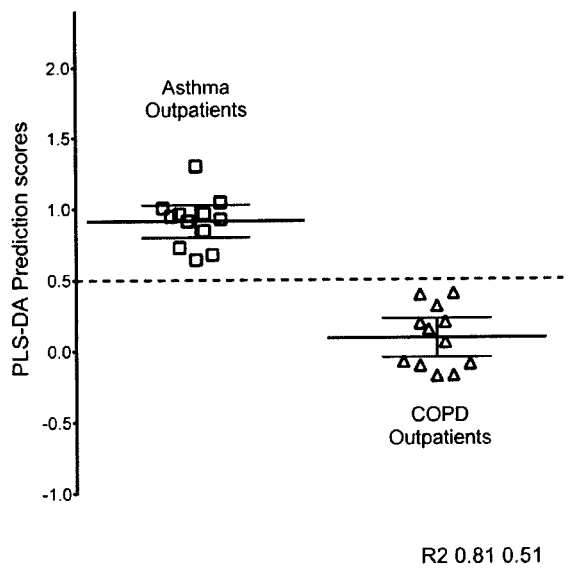
FIG. 6 depicts the PLSDA results of MS data.
Figure 7A:
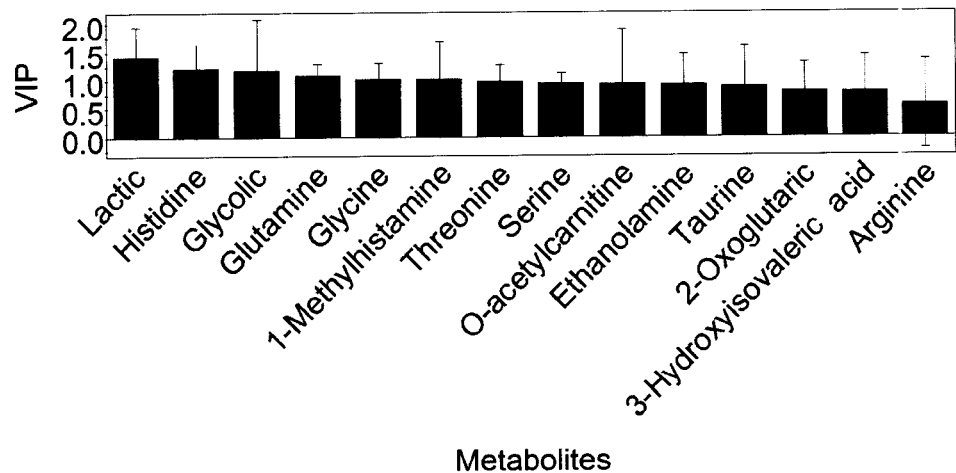
FIGS. 7A (VIP) and B (COV) depict the differences in metabolites between asthma and COPD patients outlined in Example 5.
Figure 7B:
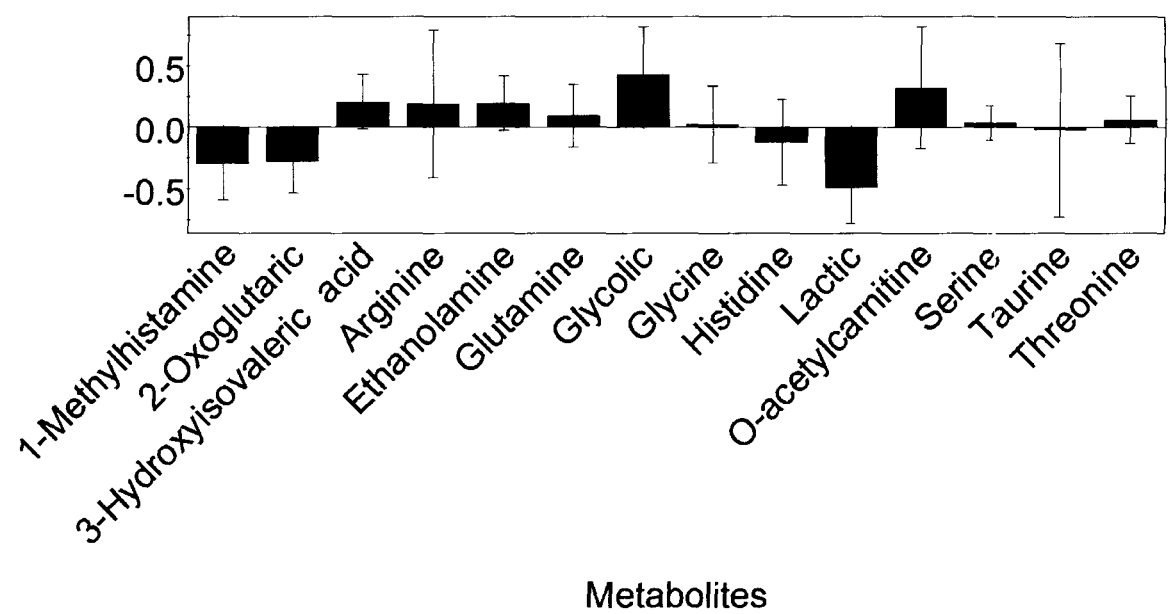

Additional patient samples with COPD (n=15) or age matched asthma (n=30) were analyzed. Similar criteria for diagnosis as were used in Examples 1 and 2 were also used in this example. Using the MS methods of Examples 3 and 4, 36 metabolites were quantified for each subject. Using PLSDA of MS data, metabolomic analysis of urine was able to differentiate asthma from COPD subjects, as is depicted in FIG. 6. FIG. 7 shows the COV and VIP. Considering the small sample size this separation is quite good.

The differences in metabolite seen in the NMR data are also similarly different using the MS methods, as can be seen in FIG. 7. The degree of difference may not be as great compared to the NMR data, but this is likely due to the smaller sample size of subjects in this example. With larger sample sizes similar statistical strength is expected. In addition, we see new metabolites of importance not seen with NMR. For example, alanine, valine, 1-methylhistamine, tyrosine, asparagine, and ethanolamine are metabolites depicted in FIG. 7 that show differences between subject groups. Thus, targeting metabolites with MS gives additional strength to the diagnosis of asthma versus COPD.

Overall, physicians require better objective tests of asthma and COPD. The present methods and models can lead to improved diagnostic capabilities. The metabolites in Table 4 are likely to be relevant in any metabolomic model which is designed to diagnosis asthma versus COPD.

These individual metabolites were identified either by NMR, MS or both. While specific numbers of metabolites were used in the Examples above, it is anticipated that at least 11 of metabolites would be sufficient to differentiate between asthma and COPD, as outlined above. In a preferred embodiment at least the following metabolites would be measured and included in the statistical analysis; 3-Hydroxyisovalerate; Glutamine; Arginine; Lactic acid; Glycolate; Tyrosine; 2-oxoglutarate; Glycine; Histidine; 1-methylhistamine; and Taurine.

TABLE 4

Metabolites identified by MS, NMR and both

| Identified by MS | Identified by MS & NMR | Identified by NMR |
| --- | --- | --- |
| 1-methyl histamine | 3-hydroxy isovaleric acid | 1 methylnicotinamide |
| 2-oxoglutaric acid | Betaine | ascorbate |
| 2-hydroxy isobutyric acid | Creatinine | choline |
| 3 Hydroxy 3 Methyl glutaric acid | Glutamine | citrate |
| 3-hydroxy butyric acid | Glycine | dimethylamine |
| Alanine | Glycolic acid | glucose |
| Asparagine | Histidine | guanidoacetate |
| Cis/Trans aconitic acids | Isoleucine | hypoxanthine |
| ethanolamine | Pantothenic acid | methanol |
| Lactic acid | Succinic acid | phe-derivative |
| Lysine | Taurine | uracil |
| O-acetylcarnitine | arginine | urea |
| Pyroglutamic acid | | xylose |
| Sarcosine | | |
| Serine | | |
| Threonine | | |
| Tryptophane | | |
| tyrosine | | |
| Valine | | |

The scope of the claims should not be limited by the embodiments as set forth in the examples herein, but should be given the broadest interpretation consistent with the description as a whole.

Although a few embodiments have been shown and described, it will be appreciated by those skilled in the art that various changes and modifications can be made to the embodiments described herein. The terms and expressions used in the above description have been used herein as terms of description and not of limitation, and there is no intention in the use of such terms and expressions of excluding equivalents of the features shown and described or portions thereof, it being recognized that the invention is defined and limited only by the claims that follow.

The teachings provided herein can be applied to other methods, not necessarily the method described herein. The elements and acts of the various embodiments described above can be combined to provide further embodiments.

These and other changes can be made to the invention in light of the above description. While the above description details certain embodiments of the invention and describes certain embodiments, no matter how detailed the above appears in text, the invention can be practiced in many ways. Details of the method may vary considerably in their implementation details, while still being encompassed by the invention disclosed herein.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification. Accordingly, the actual scope of the invention encompasses not only the disclosed embodiments, but also all equivalent ways of practicing or implementing the invention.

The above description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. The elements and acts of the various embodiments described above can be combined to provide further embodiments.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

REFERENCES

The following references are hereby incorporated by reference into this application in their entirety.
1. Jayaram L, Pizzichini M M, Cook R J, Boulet L P, Lemiere C, Pizzichini E, et al. Determining asthma treatment by monitoring sputum cell counts: effect on exacerbations. Eur Respir J 2006; 27:483-94.
2. Brightling C E, Green R H, Pavord I D. Biomarkers predicting response to corticosteroid therapy in asthma. Treat Respir Med. 2005; 4:309-16.
3. Green R H, Brightling C E, McKenna S, Hargadon B, Parker D, Bradding P, et al. Asthma exacerbations and sputum eosinophil counts: a randomised controlled trial. Lancet 2002; 360:1715-21.
4. Menezes A M, Montes de Oca M, Perez-Padilla R, Nadeau G, Wehrmeister F C, Lopez-Varela M V, et al. Increased risk of exacerbation and hospitalization in subjects with an overlap phenotype: COPD-asthma. Chest 373 2014; 145:297-304.

5. Xu E Y, Schaefer W H, Xu Q. Metabolomics in pharmaceutical research and development: metabolites, mechanisms and pathways. Curr Opin Drug Discov Devel 2009; 12:40-52.
6. Gowda G A, Zhang S, Gu H, Asiago V, Shanaiah N, Raftery D. Metabolomics-based methods for early disease diagnostics. Expert Rev Mol Diagn 2008; 8:617-33.
7. Beckwith-Hall B M, Nicholson J K, Nicholls A W, Foxall P J, Lindon J C, Connor S C, et al. Nuclear magnetic resonance spectroscopic and principal components analysis investigations into biochemical effects of three model hepatotoxins. Chem. Res. Toxicol. 1998; 11:260-72.
8. Forsythe I J, Wishart D S. Exploring human metabolites using the human metabolome database. Curr Protoc Bioinformatics 2009; Chapter 14:Unit14 8.
9. Sethi S, Mahler D A, Marcus P, Owen C A, Yawn B, Rennard S. Inflammation in COPD: implications for management. Am J Med 2012; 125:1162-70.
10. Saude E J, Obiefuna I P, Somorjai R L, Ajamian F, Skappak C, Ahmad T, et al. Metabolomic biomarkers in a model of asthma exacerbation: urine nuclear magnetic resonance. Am J Respir Crit Care Med 2009; 179:25-34.
11. Saude E J, Skappak C D, Regush S, Cook K, Ben-Zvi A, Becker A, et al. Metabolomic profiling of asthma: diagnostic utility of urine nuclear magnetic resonance spectroscopy. J Allergy Clin Immunol 2011; 127:757-64 e1-6.
12. Koller D Y, Halmerbauer G, Frischer T, Roithner B. Assessment of eosinophil granule proteins in various body fluids: is there a relation to clinical variables in childhood asthma? Clin. Exp. Allergy 1999; 29:786-93.
13. Severien C, Artlich A, Jonas S, Becher G. Urinary excretion of leukotriene E4 and eosinophil protein X in children with atopic asthma. Eur. Respir. J 2000; 16:588-92.
14. Pendharkar S, Mehta S. The clinical significance of exhaled nitric oxide in asthma. Can Respir J 2008; 15:99-106.
15. Wedes S H, Wu W, Comhair S A, McDowell K M, DiDonato J A, Erzurum S C, et al. Urinary bromotyrosine measures asthma control and predicts asthma exacerbations in children. J Pediatr 2011; 159:248-55 e1.
16. Cowan D C, Taylor D R, Peterson L E, Cowan J O, Palmay R, Williamson A, et al. Biomarker-based asthma phenotypes of corticosteroid response. J Allergy Clin Immunol 2014.
17. Nair P. Update on clinical inflammometry for the management of airway diseases. Can Respir J 2013; 20:117-20.
18. Zuo L, Koozechian M S, Chen L L. Characterization of reactive nitrogen species in allergic asthma. Ann Allergy Asthma Immunol 2014; 112:18-22.
19. Maarsingh H, Leusink J, Zaagsma J, Meurs H. Role of the L-citrulline/L-arginine cycle in iNANC nerve-mediated nitric oxide production and airway smooth muscle relaxation in allergic asthma. Eur J Pharmacol 2006; 546:171-6.
20. Boger R H. Asymmetric dimethylarginine, an endogenous inhibitor of nitric oxide synthase, explains the "L-arginine paradox" and acts as a novel cardiovascular risk factor. J Nutr 2004; 134:2842S-7S; discussion 53S.
21. Ahmad T, Mabalirajan U, Ghosh B, Agrawal A. Altered asymmetric dimethyl arginine metabolism in allergically inflamed mouse lungs. Am J Respir Cell Mol Biol 2010; 42:3-8.
22. Holguin F. Arginine and nitric oxide pathways in obesity-associated asthma. J Allergy (Cairo) 2013; 2013: 714595.
23. Holguin F, Comhair S A, Hazen S L, Powers R W, Khatri S S, Bleecker E R, et al. An association between L-arginine/asymmetric dimethyl arginine balance, obesity, and the age of asthma onset phenotype. Am J Respir Crit Care Med 2013; 187:153-9.
24. Nural S, Gunay E, Halici B, Celik S, Unlu M. Inflammatory processes and effects of continuous positive airway pressure (CPAP) in overlap syndrome. Inflammation 2013; 36:66-74.
25. Wagenmakers A J, Salden H J, Veerkamp J H. The metabolic fate of branched-chain amino acids and 2-oxo acids in rat muscle homogenates and diaphragms. Int J Biochem 1985; 17:957-65.
26. Mock N I, Malik M I, Stumbo P J, Bishop W P, Mock D M. Increased urinary excretion of 3-hydroxyisovaleric acid and decreased urinary excretion of biotin are sensitive early indicators of decreased biotin status in experimental biotin deficiency. Am J Clin Nutr 1997; 65:951-8.
27. Hofford J M, Milakofsky L, Pell S, Fish J E, Peters S P, Pollice M, et al. Levels of amino acids and related compounds in bronchoalveolar lavage fluids of asthmatic patients. Am J Respir Crit Care Med 1997; 155:432-5.
28. Gallos G, Yim P, Chang S, Zhang Y, Xu D, Cook J M, et al. Targeting the restricted alpha-subunit repertoire of airway smooth muscle GABAA receptors augments airway smooth muscle relaxation. Am J Physiol Lung Cell Mol Physiol 2012; 302:L248-56.
29. Esther C R, Jr., Peden D B, Alexis N E, Hernandez M L. Airway purinergic responses in healthy, atopic nonasthmatic, and atopic asthmatic subjects exposed to ozone. Inhal Toxicol 2011; 23:324-30.
30. Marcinkiewicz J, Kontny E. Taurine and inflammatory diseases. Amino Acids 2014; 46:7-20.
31. Lever M, Slow S. The clinical significance of betaine, an osmolyte with a key role in methyl group metabolism. Clin Biochem 2010; 43:732-44.
32. Han Y Y, Blatter J, Brehm J M, Forno E, Litonjua A A, Celedon J C. Diet and asthma: vitamins and methyl donors. Lancet Respir Med 2013; 1:813-22.
33. Sharma S, Litonjua A. Asthma, allergy, and responses to methyl donor supplements and nutrients. J Allergy Clin Immunol 2013.
34. Jung J, Kim S H, Lee H S, Choi G S, Jung Y S, Ryu D H, et al. Serum metabolomics reveals pathways and biomarkers associated with asthma pathogenesis. Clin Exp Allergy 2013; 43:425-33.
35. Schock B C, Young I S, Brown V, Fitch P S, Shields M D, Ennis M. Antioxidants and oxidative stress in BAL fluid of atopic asthmatic children. Pediatr Res 2003; 53:375-81.
36. Dillon P F, Root-Bernstein R, Robinson N E, Abraham W M, Berney C. Receptor-mediated enhancement of beta adrenergic drug activity by ascorbate in vitro and in vivo. PLoS One 2010; 5:e15130.
37. Rossman M J, Garten R S, Groot H J, Reese V, Zhao J, Amann M, et al. Ascorbate infusion increases skeletal muscle fatigue resistance in patients with chronic obstructive pulmonary disease. Am J Physiol Regul Integr Comp Physiol 2013; 305:R1163-70.
38. Hall K L, Shahrokhi S, Jeschke M G. Enteral nutrition support in burn care: a review of current recommendations as instituted in the Ross Tilley Burn Centre. Nutrients 2012; 4:1554-65.
39. Garrel D, Patenaude J, Nedelec B, Samson L, Dorais J, Champoux J, et al. Decreased mortality and infectious morbidity in adult burn patients given enteral glutamine supplements: a prospective, controlled, randomized clinical trial. Crit Care Med 2003; 31:2444-9.
40. Pouw E M, Schols A M, Deutz N E, Wouters E F. Plasma and muscle amino acid levels in relation to resting energy expenditure and inflammation in stable chronic obstructive pulmonary disease. Am J Respir Crit Care Med 1998; 158:797-801.
41. Ohtsu H. Pathophysiologic role of histamine: evidence clarified by histidine decarboxylase gene knockout mice. Int Arch Allergy Immunol 2012; 158 Suppl 1:2-6.
42. Nishiwaki F, Kuroda K, Inoue Y, Endo G. Determination of histamine, 1-methylhistamine and N-methylhistamine by capillary electrophoresis with micelles. Biomed Chromatogr 2000; 14:184-7.
43. Takei S, Shimago A, Iwashita M, Kumamoto T, Kamuro K, Miyata K. Urinary N-methylhistamine in asthmatic children receiving azelastine hydrochloride. Ann Allergy Asthma Immunol 1997; 78:492-6.
44. Stephan V, Zimmermann A, Kuhr J, Urbanek R. Determination of N-methylhistamine in urine as an indicator of histamine release in immediate allergic reactions. J Allergy Clin Immunol 1990; 86:862-8.
45. Koskela H O, Salonen P H, Niskanen L. Hyperglycaemia during exacerbations of asthma and chronic obstructive pulmonary disease. Clin Respir J 2013; 7:382-9.
46. Mirrakhimov A E. Chronic obstructive pulmonary disease and glucose metabolism: a bitter sweet symphony. Cardiovasc Diabetol 2012; 11:132.
47. Takenaka S, Kawayama T, lmaoka H, Sakazaki Y, Oda H, Kaku Y, et al. The progression of comorbidity in IL-18 transgenic chronic obstructive pulmonary disease mice model. Biochem Biophys Res Commun 2014; 445:597-601.
48. Shockcor J P, Holmes E. Metabonomic Applications in Toxicity Screening and Disease Diagnosis. Curr. Top. Med. Chem. 2002; 2:35-51.
49. Azmi J, Connelly J, Holmes E, Nicholson J K, Shore R F, Griffin J L. Characterization of the biochemical effects of 1-nitronaphthalene in rats using global metabolic profiling by NMR spectroscopy and pattern recognition. Biomarkers 2005; 10:401-16.
50. Puente-Maestu L, Perez-Parra J, Godoy R, Moreno N, Tejedor A, Gonzalez-Aragoneses F, et al. Abnormal mitochondrial function in locomotor and respiratory muscles of COPD patients. Eur Respir J 2009; 33:1045-52.
51. Yuyama S, Suzuki T. The excretion of N1-methyl-2-pyridone-5-carboxylic acid and related compounds in human subjects after oral administration of nicotinic acid, trigonelline and N1-methyl-2-pyridone-5-carboxylic acid. Adv Exp Med Biol 1991; 294:475-9.
52. Bekier E, Wyczolkowska J, Szyc H, Maslinski C. The inhibitory effect of nicotinamide on asthma-like symptoms and eosinophilia in guinea pigs, anaphylactic mast cell degranulation in mice, and histamine release from rat isolated peritoneal mast cells by compound 48-80. Int Arch Allergy Appl Immunol 1974; 47:737-48.
53. Gebicki J, Sysa-Jedrzejowska A, Adamus J, Wozniacka A, Rybak M, Zielonka J. 1-Methylnicotinamide: a potent anti-inflammatory agent of vitamin origin. Pol J Pharmacol 2003; 55:109-12.
54. Wang L, Tang Y, Liu S, Mao S, Ling Y, Liu D, et al. Metabonomic profiling of serum and urine by (1)H NMR-based spectroscopy discriminates patients with chronic obstructive pulmonary disease and healthy individuals. PLoS One 2013; 8:e65675.
55. Berglund T. Nicotinamide, a missing link in the early stress response in eukaryotic cells: a hypothesis with special reference to oxidative stress in plants. FEBS Lett 1994; 351:145-9.
56. Field H, Jr., Foa P P, Foa N L. The urinary excretion of trigonelline- and nicotinic acid-like substances in human subjects after the ingestion of trigonelline and after smoking. Arch Biochem 1946; 9:45-9.
57. McClay J L, Adkins D E, Isern N G, O'Connell T M, Wooten J B, Zedler B K, et al. (1)H nuclear magnetic resonance metabolomics analysis identifies novel urinary biomarkers for lung function. J Proteome Res 2010; 9:3083-90.
58. Vulimiri S V, Misra M, Hamm J T, Mitchell M, Berger A. Effects of mainstream cigarette smoke on the global metabolome of human lung epithelial cells. Chem Res Toxicol 2009; 22:492-503.
59. Hunninghake G M, Chu J H, Sharma S S, Cho M H, Himes B E, Rogers A J, et al. The CD4+ T-cell transcriptome and serum IgE in asthma: IL17RB and the role of sex. BMC Pulm Med 2011; 11:17.
60. Guo K, Li L. Differential 12C-/13C-isotope dansylation labeling and fast liquid chromatography/mass spectrometry for absolute and relative quantification of the metabolome. Analytical chemistry. 2009; 81:3919-32.
61. Stanislaus A, Guo K, Li L. Development of an isotope labeling ultra-high performance liquid chromatography mass spectrometric method for quantification of acylglycines in human urine. Analytica chimica acta. 2012; 750:161-72.
62. Peng J, Laurent C D S, Befus A D, Zhou R, Li L. Metabolomic profiling of bronchoalveolar lavage fluids by isotope labeling liquid chromatography mass spectrometry: a promising approach to studying experimental asthma. Metabolomics. 2014; 10:1305-17.
63. Zheng J, Li L. Fragmentation of protonated dansyl-labeled amines for structural analysis of amine-containing metabolites. International Journal of Mass Spectrometry. 2012; 316:292-9.
64. Peng J, Li L. Liquid-liquid extraction combined with differential isotope dimethylaminophenacyl labeling for improved metabolomic profiling of organic acids. Analytica chimica acta. 2013; 803:97-105.
65. Guo K, Li L. High-performance isotope labeling for profiling carboxylic acid-containing metabolites in biofluids by mass spectrometry. Analytical chemistry. 2010; 82:8789-93.
66. Tsugawa H, Tsujimoto Y, Sugitate K, Sakui N, Nishiumi S, Bamba T, et al. Highly sensitive and selective analysis of widely targeted metabolomics using gas chromatography/triple-quadrupole mass spectrometry. Journal of bioscience and bioengineering. 2014; 117:122-8.
67. Gu L, Wang X, Zhang Y, Jiang Y, Lu H, Bi K, et al. Determination of 12 potential nephrotoxicity biomarkers in rat serum and urine by liquid chromatography with mass spectrometry and its application to renal failure induced by Semen Strychni. Journal of separation science. 2014; 37:1058-66.
68. Lang R, Wahl A, Skurk T, Yagar E F, Schmiech L, Eggers R, et al. Development of a Hydrophilic Liquid Interaction Chromatography-High-Performance Liquid Chromatography-Tandem Mass Spectrometry Based Stable Isotope Dilution Analysis and Pharmacokinetic Studies on Bioactive Pyridines in Human Plasma and Urine after Coffee Consumption. Analytical chemistry. 2010; 82:1486-97.
69. Sugimoto M, Wong D T, Hirayama A, Soga T, Tomita M. Capillary electrophoresis mass spectrometry-based saliva

We claim:

1. A method of treating a respiratory disease in a subject comprising:
   a. measuring a concentration of at least 11 metabolites comprising 3-Hydroxyisovalerate, Glutamine, Arginine, Lactic acid, Glycolate, Tyrosine, 2-oxoglutarate, Glycine, Histidine, 1-methylhistamine and Taurine in a biological sample obtained from the subject to determine a subject profile;
   b. comparing the subject profile, by a statistical analysis, to a predetermined asthma disease state profile and to a predetermined Chronic Obstructive Pulmonary Disease (COPD) state profile;
   c. providing a diagnosis of an asthma disease state in the subject when the statistical analysis identifies the subject profile as more similar to the predetermined asthma disease state profile than to the predetermined COPD state profile; and
   d. upon diagnosis of the asthma disease state, administering a treatment for asthma to the subject, wherein the treatment comprises one or more of a high dose corticosteroid and a biological therapy targeting asthmatic inflammation, and wherein the treatment does not comprise an anti-muscarinic inhaler, an antibiotic, lung surgery, or lung transplantation.

2. The method of claim 1, wherein the biological sample is urine.

3. The method of claim 1, wherein the statistical analysis is a partial least squares discriminant analysis.

4. The method of claim 1, wherein the concentration of the at least metabolites is determined using one or more or a combination of spectrometric and spectroscopic techniques selected from the group consisting of mass spectrometry, liquid chromatography-mass spectrometry, gas chromatography-mass spectrometry, high performance liquid chromatography-mass spectrometry, capillary electrophoresis-mass spectrometry, raman spectroscopy, near infrared spectroscopy, and nuclear magnetic resonance spectroscopy.

5. The method of claim 1, wherein the at least 11 metabolites further comprise at least one of Pantothenic acid, Cis/Trans aconitic acids, 3 Hydroxy 3 Methyl glutaric acid, Ethanolamine, Pyroglutamic acid, Tryptophane, Creatinine, Valine, 2-hydroxy isobutyric acid, Lysine, O-acetyl-carnitine, Serine, Alanine, Isoleucine, 3-methyl adipic acid, 3-hydroxy butyric acid, Succinic acid, Sarcosine, Betaine, and Threonine.

6. A method of treating a respiratory disease in a subject comprising:
   a. measuring a concentration of at least 11 metabolites comprising 3-Hydroxyisovalerate, Glutamine, Arginine, Lactic acid, Glycolate, Tyrosine, 2-oxoglutarate, Glycine, Histidine, 1-methylhistamine and Taurine in a biological sample obtained from the subject to determine a subject profile;
   b. comparing the subject profile, by a statistical analysis, to a predetermined asthma disease state profile and to a predetermined Chronic Obstructive Pulmonary Disease (COPD)-state profile;
   c. providing a diagnosis of a Chronic Obstructive Pulmonary Disease (COPD) state in the subject when the statistical analysis identifies the subject profile as more similar to the predetermined COPD state profile than to the predetermined asthma disease state profile; and
   d. upon diagnosis of the COPD state, administering a treatment for COPD to the subject, wherein the treatment comprises one or more of an anti-muscarinic inhaler, an antibiotic, lung surgery, and lung transplantation, and wherein the treatment does not comprise a high dose corticosteroid or a biological therapy targeting asthmatic inflammation.

7. The method of claim 6, wherein the biological sample is urine.

8. The method of claim 6, wherein the statistical analysis is a partial least squares discriminant analysis.

9. The method of claim 6, wherein the concentration of the at least 11 metabolites is determined using one or more or a combination of spectrometric and spectroscopic techniques selected from the group consisting of mass spectrometry, liquid chromatography-mass spectrometry, gas chromatography-mass spectrometry, high performance liquid chromatography-mass spectrometry, capillary electrophoresis-mass spectrometry, raman spectroscopy, near infrared spectroscopy, and nuclear magnetic resonance spectroscopy.

10. The method of claim 6, wherein the at least 11 metabolites further comprise at least one of Pantothenic acid, Cis/Trans aconitic acids, 3 Hydroxy 3 Methyl glutaric acid, Ethanolamine, Pyroglutamic acid, Tryptophane, Creatinine, Valine, 2-hydroxy isobutyric acid, Lysine, 0-acetyl-carnitine, Serine, Alanine, Isoleucine, 3-methyl adipic acid, 3-hydroxy butyric acid, Succinic acid, Sarcosine, Betaine, and Threonine.

* * * * *

UNITED STATES PATENT AND TRADEMARK OFFICE
CERTIFICATE OF CORRECTION

PATENT NO. : 10,791,960 B2
APPLICATION NO. : 15/579524
DATED : October 6, 2020
INVENTOR(S) : Darryl Adamko and Anas El-Aneed Page 1 of 1

It is certified that error appears in the above-identified patent and that said Letters Patent is hereby corrected as shown below:

In the Claims

In Claim 4, Column 25, Line 33, please delete "the at least metabolites is determined using one or more or" and insert --the at least 11 metabolites is determined using one or more or--

Signed and Sealed this
Nineteenth Day of January, 2021

Andrei Iancu
*Director of the United States Patent and Trademark Office*